US011367104B1

(12) United States Patent
Lyle et al.

(10) Patent No.: US 11,367,104 B1
(45) Date of Patent: Jun. 21, 2022

(54) SYSTEMS AND METHODS FOR CAPTURING, MANAGING, AND USING RECEIPT DATA

(71) Applicant: United Services Automobile Association (USAA), San Antonio, TX (US)

(72) Inventors: Ruthie D. Lyle, Durham, NC (US); Charles Lee Oakes, III, Boerne, TX (US); Maland Keith Mortensen, San Antonio, TX (US)

(73) Assignee: UNITED SERVICES AUTOMOBILE ASSOCIATION (USAA), San Antonio, TX (US)

( * ) Notice: Subject to any disclaimer, the term of this patent is extended or adjusted under 35 U.S.C. 154(b) by 843 days.

(21) Appl. No.: 15/399,341

(22) Filed: Jan. 5, 2017

Related U.S. Application Data

(60) Provisional application No. 62/276,015, filed on Jan. 7, 2016.

(51) Int. Cl.
| | | |
|---|---|---|
| *G06Q 30/02* | (2012.01) | |
| *G06Q 30/06* | (2012.01) | |
| *G16H 50/30* | (2018.01) | |
| *G16H 20/60* | (2018.01) | |
| *G06F 19/00* | (2018.01) | |

(52) U.S. Cl.
CPC ....... *G06Q 30/0255* (2013.01); *G06F 19/328* (2013.01); *G06Q 30/0631* (2013.01); *G16H 20/60* (2018.01); *G16H 50/30* (2018.01)

(58) Field of Classification Search
CPC .... G01S 2201/01; G16H 50/30; G16H 20/60; G06Q 30/0631
See application file for complete search history.

(56) References Cited

U.S. PATENT DOCUMENTS

| | | | |
|---|---|---|---|
| 8,930,204 B1* | 1/2015 | Igoe ....................... | G06Q 30/02 705/2 |
| 10,049,598 B1* | 8/2018 | Langheier ............. | A61B 5/1118 |
| 2012/0083669 A1* | 4/2012 | Abujbara ............... | G16H 20/60 600/300 |
| 2013/0196297 A1* | 8/2013 | Anwar ................ | G06F 19/3475 434/236 |
| 2014/0214590 A1* | 7/2014 | Argue ................ | G06Q 30/0631 705/26.7 |
| 2015/0206450 A1* | 7/2015 | Wayman ............ | G06Q 30/0631 434/127 |

(Continued)

*Primary Examiner* — Christopher L Gilligan
*Assistant Examiner* — Karen A Hranek
(74) *Attorney, Agent, or Firm* — Perkins Coie LLP

(57) ABSTRACT

Methods and systems disclosed herein facilitate users to capture, manage, and use receipt data, and use the information identified in the receipts in multiple receipt data use applications. Examples of such applications are generating customized recommendations for healthier items of consumable goods or services (e.g., food or beverage) based on correlating a user's purchase habits with the user's health-related data that is monitored by a wearable device, determining insurable items from receipt line item data, creating spending forecasts geared towards budgeting and saving, facilitating donations to charities based on a percentage of price of one or more items in receipt line data, and other applications that utilize receipt data.

19 Claims, 33 Drawing Sheets

(56) References Cited

U.S. PATENT DOCUMENTS

| | | | |
|---|---|---|---|
| 2015/0363861 A1* | 12/2015 | Capel | G06Q 30/0631 |
| | | | 705/26.7 |
| 2016/0012194 A1* | 1/2016 | Prakash | G16H 50/20 |
| | | | 705/2 |
| 2016/0012512 A1* | 1/2016 | Haiby | G06Q 30/0631 |
| | | | 705/26.7 |
| 2016/0063532 A1* | 3/2016 | Loeb | G06F 40/205 |
| | | | 705/14.25 |
| 2016/0086029 A1* | 3/2016 | Dubuque | G06K 9/00536 |
| | | | 382/159 |
| 2017/0109806 A1* | 4/2017 | Adoni | G06Q 30/0631 |
| 2017/0147775 A1* | 5/2017 | Ohnemus | G16H 20/30 |

* cited by examiner

SYSTEMS AND METHODS FOR CAPTURING, MANAGING, AND USING RECEIPT DATA

CROSS-REFERENCE TO RELATED APPLICATIONS

This application is a non-provisional of and claims priority to U.S. Provisional Application No. 62/276,015, filed on Jan. 7, 2016, entitled "SYSTEMS AND METHODS FOR CAPTURING, MANAGING, AND USING RECEIPT DATA," which is hereby incorporated by reference in its entirety for all purposes.

TECHNICAL FIELD

Various embodiments of the present disclosure generally relate to receipt data. More specifically, various embodiments of the present disclosure relate to methods and systems for capturing, managing, and using line items in receipt data for use in multiple applications.

BACKGROUND

After making a purchase, a customer typically receives a receipt. Receipts can include information such as the location, time and date, amount of a purchase, and method of payment. Receipts can also include information such as the brand of a purchased item, the number of points redeemed toward a future purchase, and savings on the purchase. However, receipts are often tossed in the trash or not collected by purchasers.

BRIEF DESCRIPTION OF THE DRAWINGS

Embodiments of the present disclosure will be described and explained through the use of the accompanying drawings in which.

DETAILED DESCRIPTION

Figure 1:
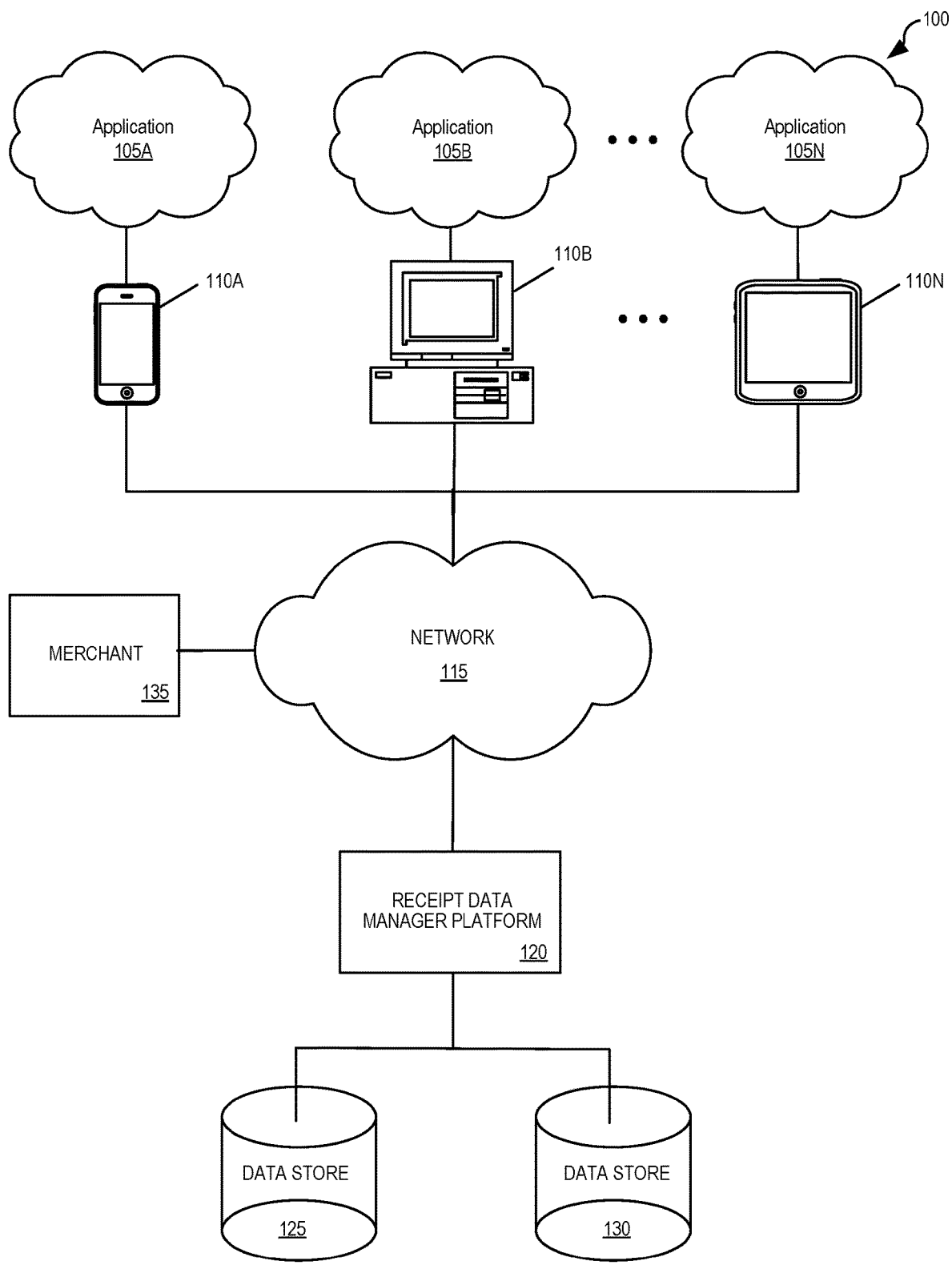
FIG. 1 illustrates an example of a network-based operating environment in accordance with various embodiments of the disclosure.

Various embodiments of the present disclosure generally relate to receipt data. More specifically, various embodiments of the present disclosure relate to methods and systems for capturing, managing, and using line items in receipt data for use in multiple applications.

Receipt data may be used, for example, to monitor and improve health. Conventionally, an average user who wishes to monitor their eating habits and lifestyle has to manually enter information pertaining to their diets or exercise regimen into some kind of a mobile or desktop application managed by a third party. In some situations, users have to weigh their portion sizes or calories to determine what to enter in these programs. In many scenarios, a user has no knowledge of what to enter or whether he or she is entering the correct calorific information. This can lead to erroneous monitoring so that a user might not benefit from these programs.

Receipt data may be used in managing the user's health by generating customized recommendations for healthier items of consumable goods or services (e.g., food or beverage). For example, the disclosed system can identify (from the receipt data of a user's purchase at a grocery store) that a user has purchased a first brand of cereal which has a higher sugar content than a second brand of cereal. Upon detecting the purchase, and in view of monitoring the user's blood sugar readings, the system can provide personalized recommendations to the user to swap the first cereal with the second cereal. In some embodiments, the monitored-health data can be shared with health services providers, life insurance providers, and medical insurance providers. Such information may be used by insurance providers to lower rates for the user (e.g., a health insurance provider may reduce the user's premium costs for improved behavior).

In another example, insurable items can be determined from receipt line item data, and insurance policies can be offered for the insurable items. For example, based on receipt information identifying that a user has purchased filters for an air conditioner, the system can determine that a user has an air conditioner, and accordingly offer an insurance policy that covers the air conditioner. In another example, if a user wishes to insure a television (detected by the system as having purchased by the user based on a receipt) in a living room of the user, the system can request from the user an image of the television. The system can scan the image submitted by the user to identify additional insurable items (e.g., home theater, couch, etc.). The insurance policy can be a new policy or an extension of an existing policy.

Other examples of using receipt data include creating forecasts geared toward budgeting, saving and facilitating donations to charities based on a percentage of price of one or more items in receipt line data.

This disclosure describes receipt data use systems and methods designed to manage information mined from receipts of purchases of goods or services. Various embodiments may provide one or more of the following technological improvements: 1) correlating receipt data of purchases of consumable goods or services with health-related data obtained from wearable devices attached to a user's body; 2) detecting additional insurable items using receipt data and scanning images and other media that display a first insurable item in an operating environment; 3) a receipt data capture process involving multiple channels (SMS messages, emails, MMS messages, images taken by dedicated mobile application programs) for determining insurable items of a user reflected in the receipt data, and for aggregating information pertaining to the insurable items in a user profile in the insurance database.

As used herein, the term "user" is not limited to private individuals but can include small and large business owners. More generally, the term "user" includes any person or entity that uses the system. Moreover, the entity that operates the system disclosed herein can be any kind of entity, public or private, including banks, insurance companies, and financial institutions. Such an entity can also be an issuer of one or more credit cards. In the discussions herein, the term "card" or "credit card" is used for example purposes. Broadly, these terms can be applied in the context of any "financial instrument" and are interchangeable.

In the following description, for the purposes of explanation, numerous specific details are set forth in order to provide a thorough understanding of embodiments of the present disclosure. However, it will be apparent, on reading the disclosure, to one skilled in the art, that embodiments may be practiced without some of these specific details.

Moreover, the techniques introduced here can be embodied as special-purpose hardware (e.g., circuitry), as programmable circuitry appropriately programmed with software and/or firmware, or as a combination of special-purpose and programmable circuitry. Hence, embodiments may include a machine-readable medium having stored thereon instructions that may be used to program a computer (or other electronic devices) to perform a process. The machine-readable medium may include, but is not limited to, floppy diskettes, optical disks, compact disc read-only memories (CD-ROMs), magneto-optical disks, ROMs, random access memories (RAMs), erasable programmable read-only memories (EPROMs), electrically erasable programmable read-only memories (EEPROMs), magnetic or optical cards, flash memory, or other type of media/machine-readable medium suitable for storing electronic instructions.

FIG. 1 illustrates an example of a network-based operating environment 100 in which some embodiments of the present disclosure may be used. As illustrated in FIG. 1, operating environment 100 may include applications 105A-105N running on one or more computing devices 110A-110M (e.g., a mobile device; a mobile phone; a telephone; a tablet computer; a mobile media device; a mobile gaming device; a vehicle-based computer; a dedicated terminal; a public terminal, desktop, or laptop computer; a kiosk; or wearable devices such as a smartwatch, an electronic wrist band, an electronic exercise band). In some embodiments, applications 105A-105N may be stored on one or more computing devices 110A-110M or may be stored remotely on a server (in the "cloud"). These computing devices 110A-110M can include mechanisms for receiving and sending traffic by connecting through network 115 to receipt data manager platform 120, merchant 135, and data stores 125 and 130.

The network-based operating environment 100 also includes merchant 135 connected via network 115 to receipt data manager platform 120. Merchant 135 can be a physical store, supermarket, or an online store.

Computing devices 110A-110M may be configured to communicate via the network 115 with receipt data manager platform 120. In some embodiments, computing devices 110A-110M can submit information (e.g., an electronic receipt, a purchase context of a user when the user is shopping online or at a store, or a user's health-related data based on monitoring a user's health directly or via a wearable device attached to the user's body) to receipt data manager platform 120 and run one or more applications 105A-105N with customized content retrieved by receipt data manager platform 120 and data stores 125 and 130. For example, computing devices 110A-110M can execute a browser application or a customized client to enable interaction between the computing devices 110A-110M, receipt data manager platform 120, and data stores 125 and 130. In some embodiments, users can provide to receipt data manager platform 120 their preferences for certain goods or services, information pertaining to their insurable items, budgets in various categories/subcategories of goods or services via computing devices 110A-110M (e.g., via a web portal or a mobile application program). In some embodiments, computing devices 110A-110M are configured to provide a purchase context of a user via a localization mechanism (e.g., via a sensor coupled to one or more of these devices).

Network 115 can be any combination of local area and/or wide area networks, using wired and/or wireless communication systems. Network 115 can be or could use any number of protocols/technologies, including Ethernet, IEEE 802.11 or Wi-Fi, worldwide interoperability for microwave access (WiMAX), cellular telecommunication (e.g., 3G, 4G, 5G), CDMA, cable, digital subscriber line (DSL), etc. Similarly, the networking protocols used on network 115 may include multiprotocol label switching (MPLS), transmission control protocol/Internet protocol (TCP/IP), User Datagram Protocol (UDP), hypertext transport protocol (HTTP), simple mail transfer protocol (SMTP) and file transfer protocol (FTP). Data exchanged over network 115 may be represented using technologies, languages, and/or formats, including hypertext markup language (HTML) or extensible markup language (XML). In addition, all or some links can be encrypted using conventional encryption technologies such as secure sockets layer (SSL), transport layer security (TLS), and Internet Protocol security (IPsec).

Receipt data manager platform 120 can be running on one or more servers and can be used to receive receipt data of purchases of goods or services; identify the purchase context of a user during and/or after a user's purchase of goods or services; generate recommendations that are optimized or personalized on a per-user basis; determine insurability of one or more insurable items; detect insurable items based on scanning an image of an insurable item; generate mapping data as an outcome of correlation between a user's monitored health-related data and a user's purchase habits, as reflected in the receipt data; generate savings and budgeting data based on better-price, better-quality, or healthy variants of goods or services; provide recommendations to a user or computing device directly, or to a mobile application running on the computing devices 110A-110N; continuously monitor a user's health with the help of one or more computing devices 110A-110N; make recommendations on when and where to purchase regularly purchased items; and track and/or perform other activities. In some embodiments, receipt data manager platform 120 includes various data processing and analytic tools to identify savings opportunities for a user. In some embodiments, receipt data manager platform 120 is a server.

Data stores 125 and 130 can be used to manage storage and access to user data such as user profiles, user financial and personal data, data received from receipts of purchases of goods or services, data pertaining to one or more insurable items, data pertaining to third parties, and other information. Data stores 125 and 130 may be a data repository of a set of integrated objects that are modeled using classes defined in database schemas. Data stores 125 and 130 may further include flat files that can store data. Receipt data manager platform 120 and/or other servers may collect and/or access data from the data stores 125 and 130. Information provided by users can be stored in data stores 125 and 130.

Figure 2:
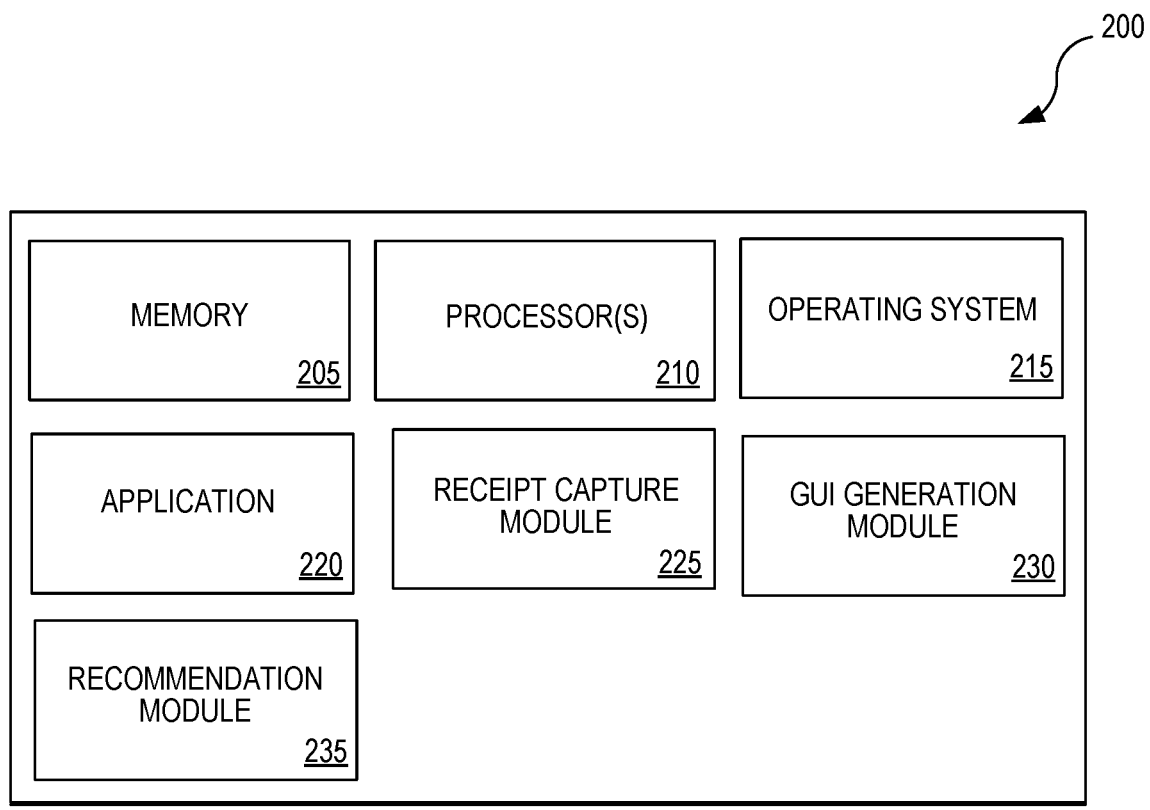
FIG. 2 illustrates various components of a computing device of a user that may be used in accordance with one or more embodiments of the disclosure.

FIG. 2 illustrates a set of components 200 within computing device 110 according to one or more embodiments of the present disclosure. According to the embodiments shown in FIG. 2, computing device 110 can include memory 205, one or more processors 210, operating system 215, application 220, receipt capture module 225, GUI generation module 230, and recommendation module 235. Other embodiments of the present disclosure may include some, all, or none of these modules and components, along with other modules, applications, and/or components. Still yet, some embodiments may incorporate two or more of these modules and components into a single module and/or associate a portion of the functionality of one or more of these modules with a different module. For example, in one embodiment, application 220 and receipt capture module 225 can be combined into a single component. In another example, receipt capture module 225 and recommendation module 235 can be combined into a single component.

Memory 205 can be any device, mechanism, or populated data structure used for storing information. In accordance with some embodiments of the present disclosure, memory 205 can encompass, but is not limited to, any type of volatile memory, nonvolatile memory, and/or dynamic memory. For example, memory 205 can be random access memory, memory storage devices, optical memory devices, magnetic media, floppy disks, magnetic tapes, hard drives, SIMMs, SDRAM, DIMMs, RDRAM, DDR RAM, SODIMMs, EPROMs, EEPROMs, compact discs, DVDs, and/or the like. In accordance with some embodiments, memory 205 may include one or more disk drives, flash drives, one or more databases, one or more tables, one or more files, local cache memories, processor cache memories, relational databases, flat databases, and/or the like. In addition, those of ordinary skill in the art will appreciate many additional devices and techniques for storing information that can be used as memory 205.

Memory 205 may be used to store instructions for running one or more applications or modules on processor(s) 210. For example, memory 205 could be used in one or more embodiments to house all or some of the instructions needed to execute the functionality of operating system 215, application 220, receipt capture module 225, GUI generation module 230, and recommendation module 235.

Operating system 215 can provide a software package that is capable of managing the hardware resources of computing device 110. Operating system 215 can also provide common services for software applications running on processor(s) 210. In accordance with various embodiments, operating system 215 can coordinate resources for multiple applications 220 that allow a user to access and interact with receipt data manager platform 120. For example, application 220 can include an application for financial services (e.g., a mobile wallet), a money transfer application, a social networking application, and a gaming application.

Application 220 can access a server and/or a platform associated with an organization (e.g., receipt data manager platform 120) to, for example, receive recommendations for lower-priced goods or services or, in some instances, better quality goods and services (e.g., received from recommendation module 235) and provide the recommendations to the user. In some embodiments, recommendations are sent by push notifications to a user through a mobile application associated with the receipt data manager platform 120. In some embodiments, such mobile application can run in the background of a user's mobile device such that the user does not need to actively select the mobile application. Application 220 interacts, for example, with recommendation module 235, GUI generation module 230, memory 205, and operating system 215.

Receipt capture module 225 captures receipt information for various goods or services purchased by a user. For example, a user can directly (i.e., from within a mobile application and without selecting a standalone camera), take an image of one or more receipts. In some embodiments, a user can take an image of a receipt using any type of camera (e.g., video camera, cell phone camera, polaroid camera) and then email, upload, or send by MMS messaging, the image of the receipt to the receipt data manager platform 120. In some embodiments, receipts can be provided to the user electronically from the merchant (e.g., via email, sms text). Receipt data may include the purchased items, a location of the purchase, merchant, savings on the purchased items, total amount of the purchase, a phone number of the merchant, brands of the items purchased, coupons or rewards points used, and a credit card, or portions of a credit card, used for the purchase.

In some embodiments, receipt capture module 225 is able to receive location information relating to a user's geographical location (e.g., via a localization mechanism). The localization mechanism can, for example, include a sensor coupled to a mobile device of the user and can utilize one or more of the following, or other, types of wireless signals: Wi-Fi, RFID, NFC, satellite, cellular, and Bluetooth. For example, the mobile application can detect a wireless communication signal broadcasted by a device located external to the mobile device, where the wireless communication signal is a Bluetooth Low Energy (BLE) signal and the device is a beacon. Information relating to a user's geographical location can be sent to receipt data manager platform 120 for determining a store or merchant location where a user purchased goods or services. Location information can be beneficial when a store or merchant location is not easily identified from, or is not included in, the receipt data.

In some scenarios, a user's geographical location is continuously monitored, and information pertaining to the user's geographical location is sent to receipt data manager platform 120. In some embodiments, receipt capture module 225 can electronically scan (e.g., using optical character recognition technology) receipts and convey the scanned receipts to the receipt data manager platform 120. In some embodiments, an image of the receipt is captured and the scanning is performed by the receipt data manager platform 120. Examples of digital receipts displayed by receipt capture module 225 are shown in FIGS. 9, 10, 25, 30, and 31.

GUI generation module 230 can generate one or more GUI screens that allow for interaction with a user. In at least one embodiment, GUI generation module 230 generates a graphical user interface receiving and/or conveying information (e.g., provided by recommendation module 235) to the user.

Figure 14:
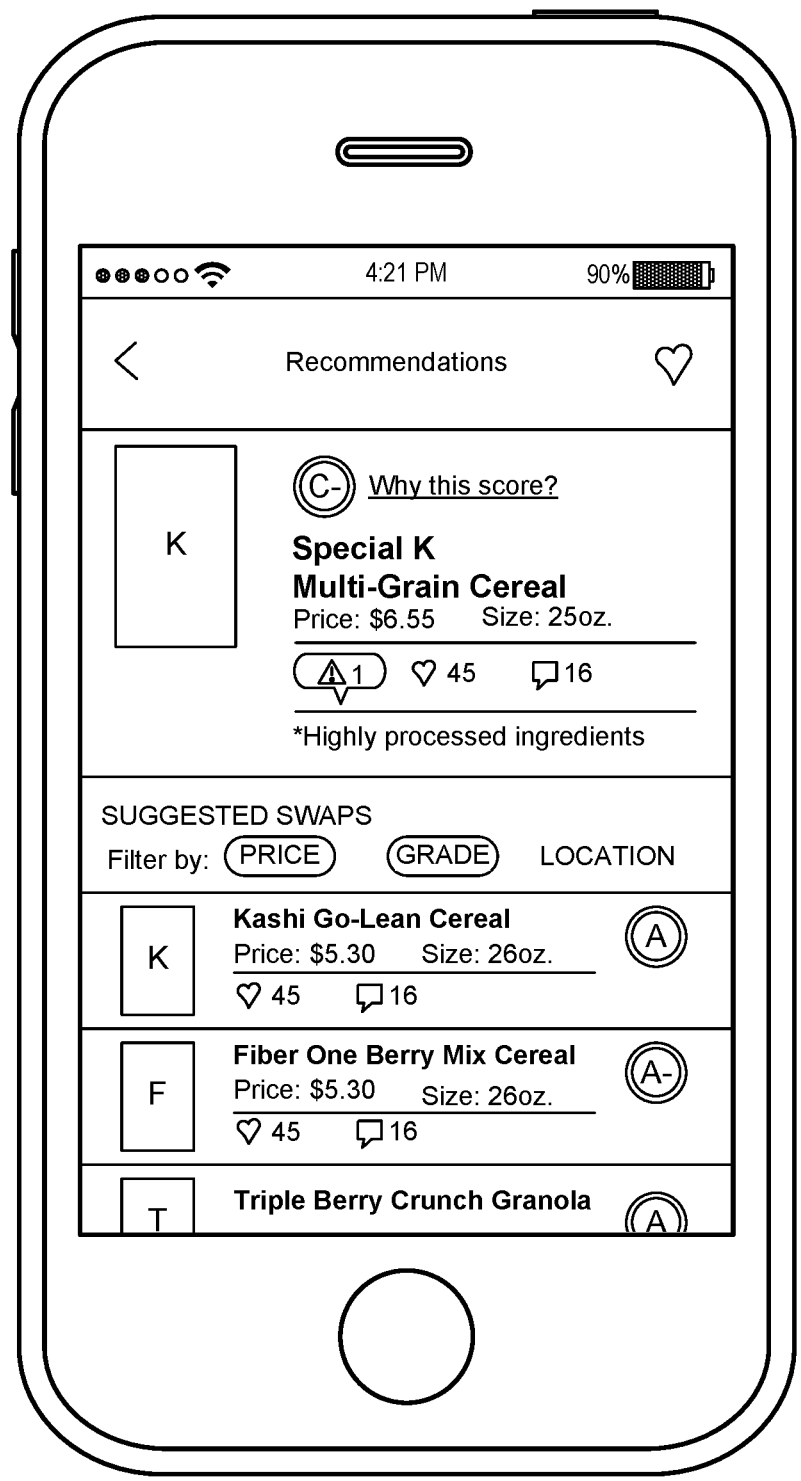
Figure 15:
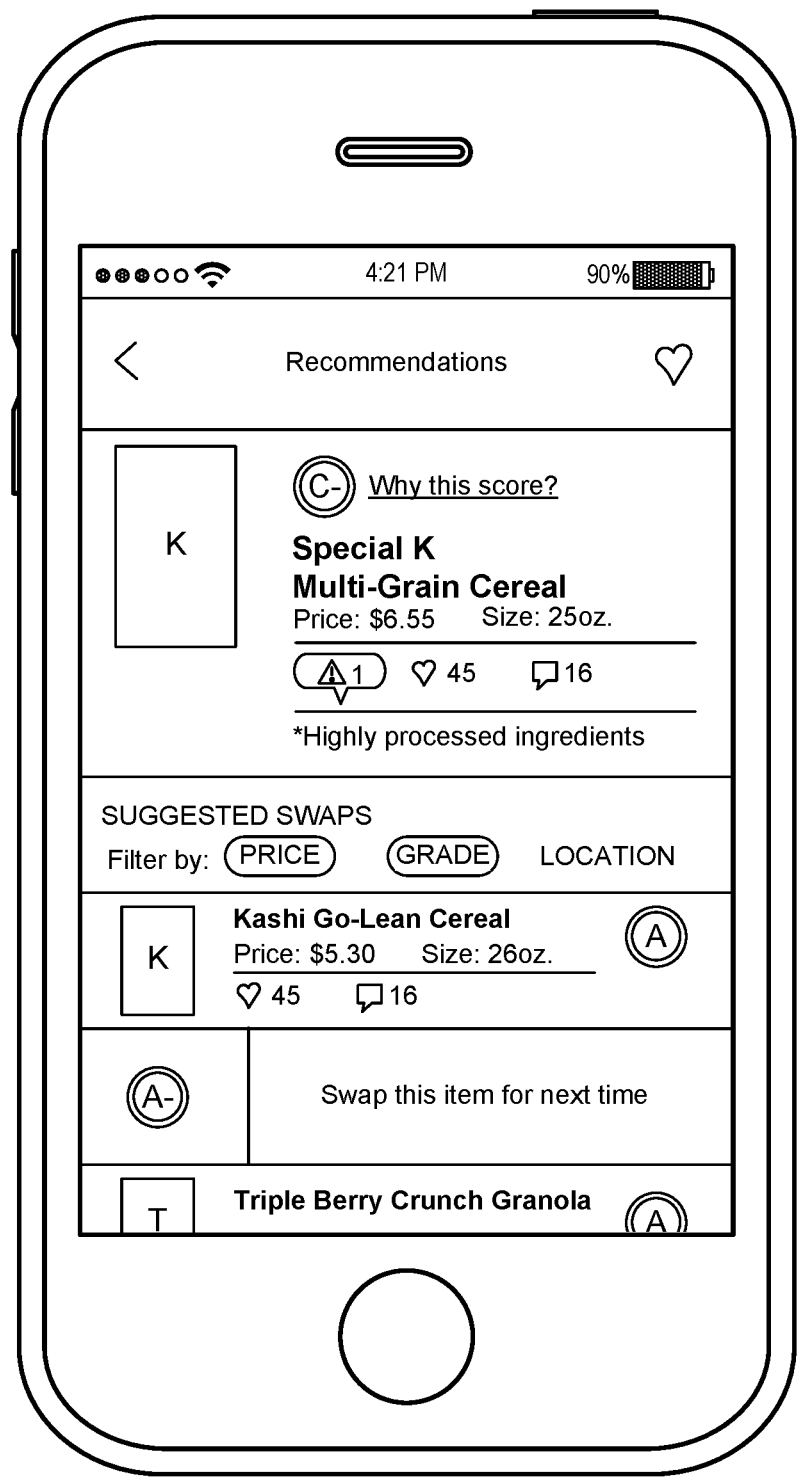

Recommendation module 235 receives from receipt data manager platform 120 recommendations (as shown in FIGS. 14 and 15) or other indications of the goods or services purchased by a user, information pertaining to the store in which the purchase was made, recommendations for lower-priced goods or services or better quality goods or services, savings captured by a user, analytics (e.g., breakdown by categories and sub-categories) pertaining to the goods or services purchased by a user, a financial target budgeted by the user for various categories and sub-categories of goods or services, and a relative difference between the financial target and a total amount spent by the user per category and/or sub-category.

Figure 11:
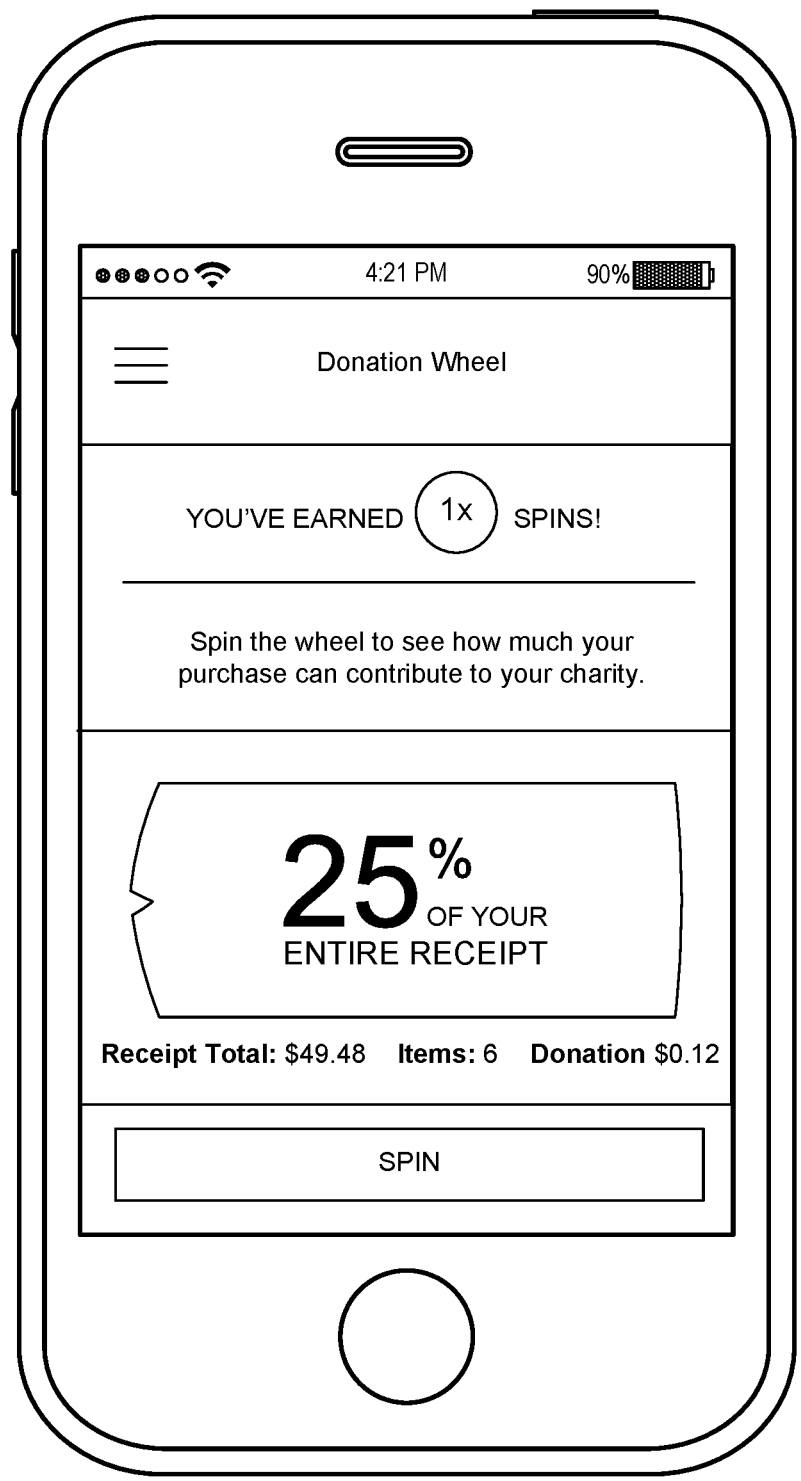

In some embodiments, recommendation module 235 receives indications of various insurable items that can be covered under a user's home insurance policy, rental insurance policy, appliance insurance policy, or business owner insurance policy. In some embodiments, recommendation module 235 provides information relating to one or more charities to which a user can donate should the user choose. In some embodiments, recommendation module 235 gamifies a user's charitable contribution. For example, recommendation module 235 can display a spinning wheel for a user to interact, via the GUI, as shown in FIG. 11. The user can spin the wheel and choose to contribute to a charity based on a percentage of one or more receipts or the amount displayed on the wheel. The one or more receipts that determine the user's charitable contributions can be selected by the user, the receipt data manager platform 120, or both. In some embodiments, a user can share information relating to the charitable contributions on a social media network.

Thus, recommendation module 235 can invoke one or more applications in application 220 for sharing recommendations and information. In some embodiments, the entity associated with receipt data manager platform 120 matches the user's donation amount. In some embodiments, a user can customize the interface of the mobile application program associated with the receipt data manager platform 120 to indicate the top categories of interest to the user. Users, for example, can rank or reorder categories.

Figure 3:
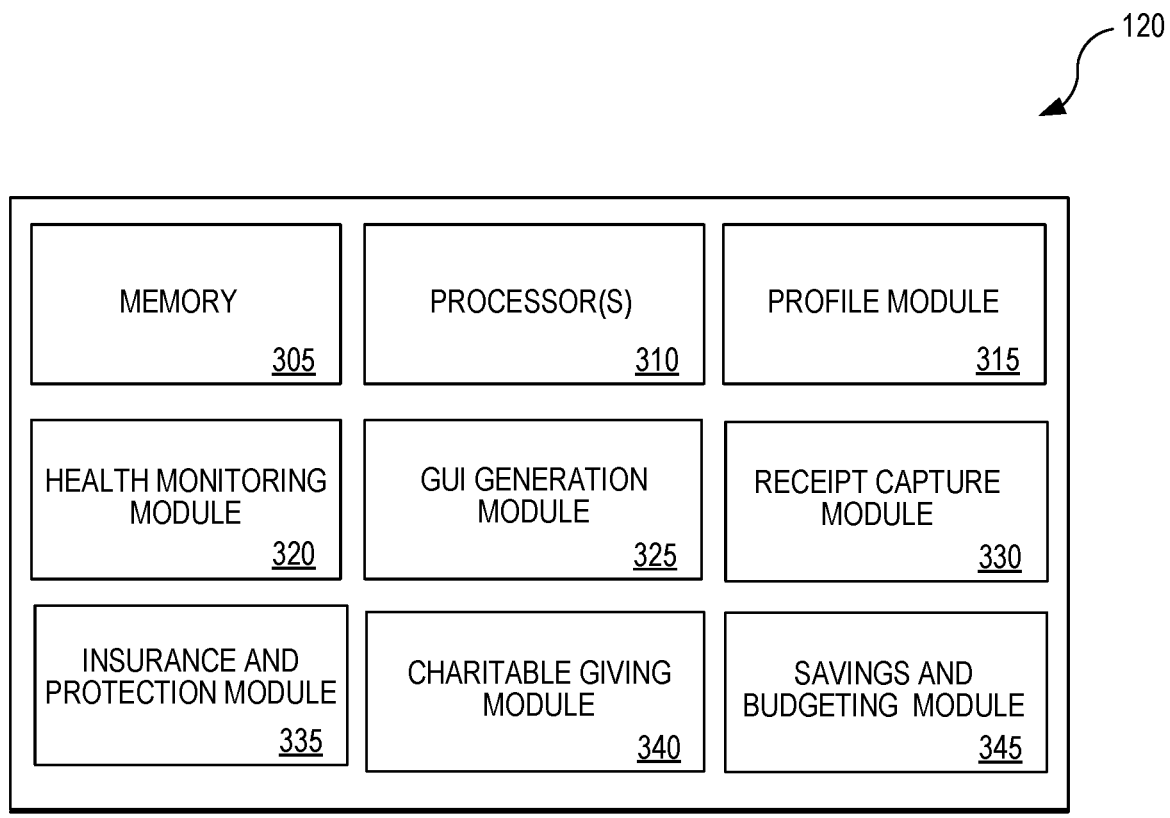
FIG. 3 illustrates various components of a receipt data manager platform that may be used in accordance with various embodiments of the present disclosure.

FIG. 3 illustrates a set of components within receipt data manager platform 120 according to one or more embodiments of the present disclosure. According to the embodiments shown in FIG. 3, receipt data manager platform 120 can include memory 305, one or more processors 310, profile module 315, health monitoring module 320, GUI generation module 325, receipt capture module 330, insurance and protection module 335, charitable giving module 340, and savings and budgeting module 345. Other embodiments of the present invention may include some, all, or none of these modules and components, along with other modules, applications, and/or components. Still yet, some embodiments may incorporate two or more of these modules and components into a single module and/or associate a portion of the functionality of one or more of these modules with a different module.

Memory 305 can be any device, mechanism, or populated data structure used for storing information as described above for memory 205. Memory 305 may be used to store instructions for running one or more applications or modules on processor(s) 310. For example, memory 305 could be used in one or more embodiments to house all or some of the instructions needed to execute the functionality of profile module 315, health monitoring module 320, GUI generation module 325, receipt capture module 330, insurance and protection module 335, charitable giving module 340, and savings and budgeting module 345.

Profile module 315 can create and maintain profiles for the users of receipt data manager platform 120 or individuals or businesses associated with the user. Profiles can include a user's personal data; insurance data for various types of insurance policies, such as home insurance, rental insurance, business insurance, and health insurance; bank/financial institution data; credit/debit card data; preferences of a user for goods or services; analytics collected from prior purchases made by a user; one or more charities preferred by a user; and health data of a user or a user's family members. Personal data of a user can include a name, address, phone number, email address, class of a user identifying whether the user is a residential user or a business owner, and insurance policies.

In some embodiments, a user can select or rank (e.g., via a GUI on a mobile application or a desktop application) various categories or subcategories of interest to him or her. Examples of categories can include entertainment, food, and clothing. A category, for example, food, can be further broken into subcategories such as dining out, groceries, snacks, and coffee. Further, a subcategory such as groceries includes the various grocery items such as produce/fruits/processed food, meats, etc. purchased by a user. Thus, embodiments of the present disclosure facilitate classifying a user's purchased goods or services into various categories and sub-categories. The categories and sub-categories can be predetermined or they can be user-specified. Profile module 315 can query a networked database to retrieve profile information of users. Such profile information can be stored in the "cloud," or physically coupled to profile module 315.

Health monitoring module 320 can monitor and aggregate health-related data of a user, or individuals or businesses associated with the user. For example, health monitoring module 320 can monitor and receive a user's vital health data (e.g., blood pressure, heart rate, body temperature, height, weight). Such data can be sent by a consumer-wearable device attached to a user's body. The consumer-wearable device can be, for example, a band or necklace attached to a user's body. In some instances, the consumer-wearable device can be a user's mobile phone. The consumer-wearable device can send vital health data or fitness/physical exercise data (e.g., number of steps walked or number of miles ran) directly to health monitoring module 320, or it can send such data to a user's mobile device, which then conveys this data to the health monitoring module 320.

In some embodiments, receipt data manager platform 120 correlates data collected by health monitoring module 320 with data collected from receipts of a user's purchased goods or services. For example, a user's cholesterol readings, monitored and collected by health monitoring module 320, can be correlated with purchases made by a user at a grocery store, or with meals purchased at restaurants and bars, to determine the relationship (e.g., mappings) between a user's health and the user's purchase habits. Such correlation data can, in some instances, be used to offer discounts on health insurance and/or life insurance policies.

In some embodiments, data collected by health monitoring module 320 can be used by receipt data manager platform 120 to generate and provide personalized recommendations to the user. For example, a user might have purchased a first brand of cereal that has a higher sugar content than a second brand of cereal. Upon detecting the purchase, and in view of the user's blood sugar readings monitored by health monitoring module 320, receipt data manager platform 120 can provide personalized recommendations (e.g., by communicating with an application running on the user's mobile phone) to the user to swap the first cereal with the second cereal. For example, FIGS. 14 and 15 illustrate "Special K Multi-Grain Cereal" as having highly processed ingredients. Hence, a suggestion is offered to the user to swap that cereal with any of "Kashi Go-Lean Cereal," "Fiber One Berry Mix Cereal," or "Triple Berry Crunch Granola." In some embodiments, receipt data manager platform 120 can identify or build a grocery list with appropriate nutrients based on workouts or diets. Additionally, recipes can be created based on workouts monitored by health monitoring module 320 and/or items that receipt data manager platform 120 knows the user has purchased via the receipt data.

Figure 16:
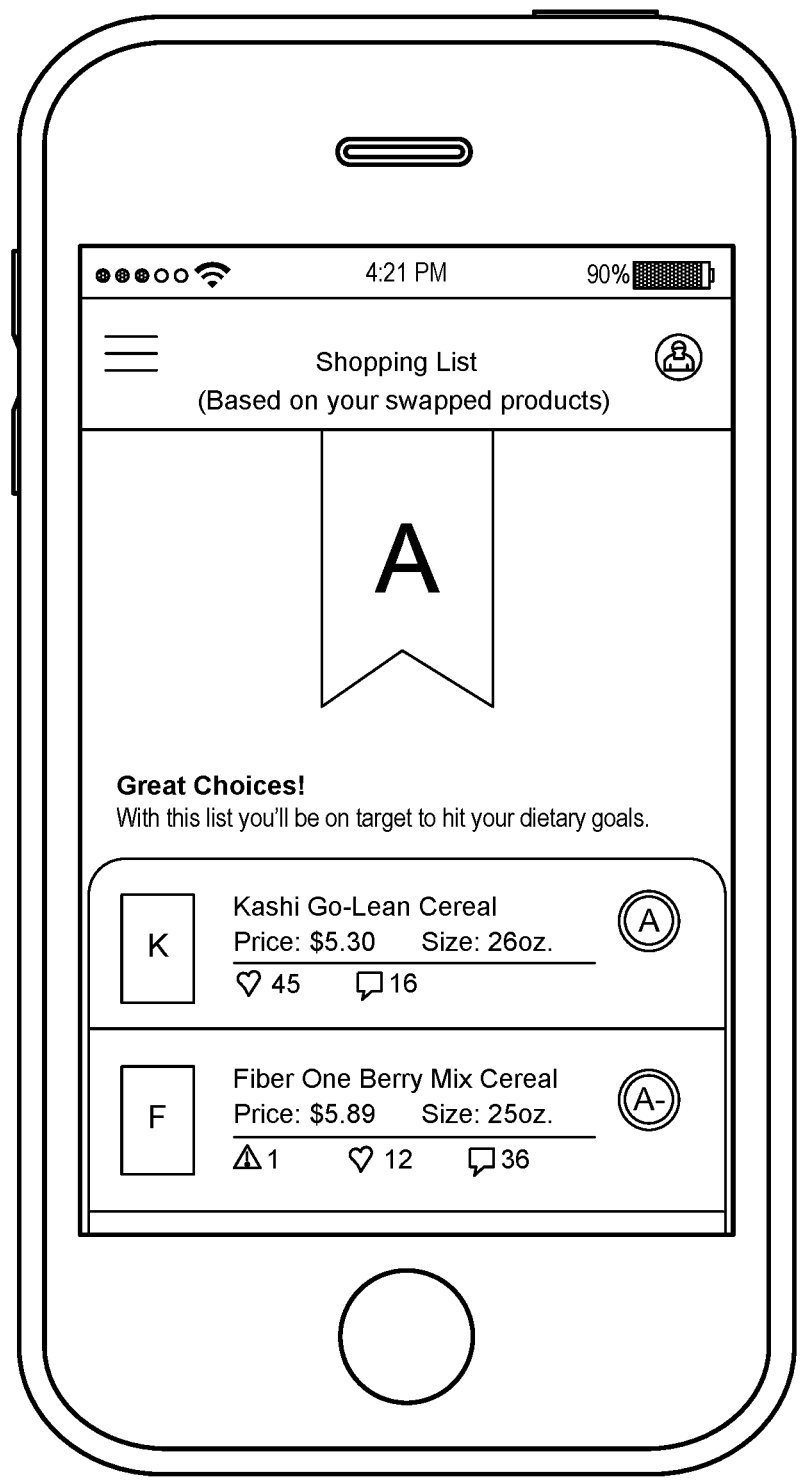

In a further example, as shown in FIGS. 15 and 16, a user can swap items on a shopping list to view the resulting revised recommendations provided by health monitoring module 320. In some instances, the user is also provided further information, such as a merchant or store location where the user can purchase the second brand of cereal, an associated price, and coupons/discounts provided by the manufacturer or retailer, if any. In some scenarios, the personalized recommendations can be in the form of brand advertisements and can optionally include coupons and rebates. Thus, in some embodiments, the receipt data manager platform 120 provides customized recommendations to the user for goods and services that are optimized, based on a user's health data received from health monitoring module 320.

In some embodiments, health monitoring module 320 tracks a user's exercise levels (e.g., neurology data, number of steps walked, number of calories burned, number of miles ran/biked/swam, amount of weight lifted during a workout, number of repetitions and sets of an exercise performed, a time duration of the exercise, a type of exercise, heartrate, body weight, body density, and pulse). In some embodiments, health monitoring module 320 can receive real-time or near real-time data corresponding to a user's health and fitness levels, either directly entered by a user or tracked by a wearable device attached to the user's body. In some embodiments, the data is first assimilated by the user's wearable device, which then conveys it to health monitoring module 320. In some embodiments, the computing device of the user receives the heath data (e.g., takes the user's pulse) or receives the health data from the wearable device and conveys to health monitoring module 320.

In some embodiments, receipt data manager platform 120 can generate analytics and parameters based on data collected by health monitoring module 320. Examples of such analytics and parameters can include body mass index (BMI), and calories consumed per unit body weight. In some embodiments, health monitoring module 320 can, based on the correlation data, generate a custom list for a user, including healthy food and beverage options, exercise options, and options for leading a healthy, stress-free life.

In some embodiments, health monitoring module 320 can generate a custom list in collaboration with savings and budgeting module 345. In some embodiments, generating a custom list for the user is based on analysis of historical purchase habits of the user, which is collected from prior receipts of consumable items of goods or services, e.g., as detected by receipt capture module 330. In some embodiments, health monitoring module 320 can communicate with a user's medical provider and/or health insurance provider to provide or receive health-related data of a user. Such data can be used in generating a user's health-related analytics and parameters.

In some embodiments, health monitoring module 320 can score a user based on items of foods or beverages purchased by the user, as shown in FIGS. 13, 14, 15, and 16. For example, upon scanning a receipt a first time, receipt capture module 330 detects that a user purchased a gallon of whole milk from the grocery store. Further, health monitoring module 320, which has been monitoring the health of this user identifies the user as being obese. In such scenarios, health monitoring module 320 can recommend that the user switch to fat free milk. If the user buys fat free milk at the grocery store a next time, the purchase is detected by receipt capture module 330, which then informs the health monitoring module 320 of the line item (i.e., information pertaining to the purchase) in the user's receipt. Upon detecting that the user has switched to a healthier option (e.g., fat free milk), health monitoring module 320 can reward the user with points that are reflective of healthy choices made by the user. A user can accumulate such points and the score can be communicated to a user's life insurance provider, health provider, or health insurance provider.

In some embodiments, health monitoring module 320 can monitor in real-time or near real-time as a user is purchasing goods or services at a store to detect or identify a purchase context of the goods or services. For example, health monitoring module 320 can detect that a user who is at a supermarket is in close proximity to a "healthy food choices" section. Such detection can be based on a localization mechanism. The localization mechanism can, for example, include a sensor coupled to a mobile device (e.g., mobile phone) of the user and can utilize one or more of the following, or other, types of wireless signals, such as Wi-Fi, RFID, NFC, satellite, cellular, and Bluetooth. For example, the mobile application running on a user's mobile phone can detect a wireless communication signal broadcasted by a device located at the entrance and exit of an aisle in the "healthy food choices" section (i.e., at a location external to the user's mobile device), where the wireless communication signal is a Bluetooth Low Energy (BLE) signal, and the device is a beacon. The purchase context associated with a user's purchase of goods or services can include a time; a location of the user, goods or services; and the types of goods or services.

GUI generation module 325 is capable of generating one or more GUI screens that allow for interaction with a user. In at least one embodiment, GUI generation module 325 generates a graphical user interface receiving and/or conveying information to the user. For example, GUI generation module 325 may display one or more receipts corresponding to goods or services purchased by a user; recommendations to use one or more goods or services for financial savings or for health-related reasons, or to suggest better quality goods or services; and recommendations to insure appliances or items purchased by a user, as detected by receipt capture module 330.

Receipt capture module 330 collects data from one or more receipts associated with a user's purchase of goods or services. Receipt capture module 330 can capture receipts from multiple channels, such as a mobile application running on a user's mobile device, an email sent by a user, an MMS or SMS sent by a user, and the like. In some embodiments, receipt capture module 330 can receive receipts directly from a merchant or store (e.g., a point of sale device). In some embodiments, receipt capture module 330 can electronically scan (using optical character recognition technology) receipts and save information obtained from parsing the receipts in one or more networked databases. In some embodiments, an image of the receipt is received as an image file. In some embodiments, a receipt is received as a Word document or a PDF document.

Receipt capture module 330 extracts, after parsing, information relating to the purchase. Examples of receipt information include the name of a store or a merchant location; a type, price and quantity of goods or services; a brand name; or a distributor name. In some scenarios, a receipt can, include an abbreviated or a shortened name rather than a complete description of the purchased goods or services. In such scenarios, receipt capture module 330 can identify such goods or services based on a lookup table that indicates a full description corresponding to the shortened name. In situations where the full description cannot be identified, receipt data manager platform 120 can query the subject merchant or store involved in the purchase transaction, or a third party that can provide lookup services for the full description, given the shortened name.

In some embodiments, receipt data manager platform 120 can generate business analytics based on the receipt data, which can be used for business development. For example, if receipt capture module 330 determines that 3 million Pepsi® soft drink purchasers are located in a geographical area, then this data can be shared with a competitor, Coke® soft drink, which, in turn, can provide incentives to attract potential purchasers. Similarly in a set of users with a prescribed affinity (e.g., employees of the same company), incentives to attract potential purchasers could be provided (e.g., discounts for all employees of a certain company based on receipt data). In some embodiments, receipt capture module 330 keeps track of various merchant locations, and the goods or services purchased by a user from these locations. This is beneficial in scenarios where there is a recall on any item by a manufacturer, retailer, or distributor. In such scenarios, receipt data manager platform 120 can monitor public notices of recalls and, accordingly, notify a user of such recalls without the user having to manually keep track of any recalls. Embodiments of receipt capture module 330 can collect data from any receipt (without limitation), from any merchant selling any kind of goods or services. Examples of digital receipts captured by receipt capture module 330 are shown in FIGS. 9, 10, 13, 14, 15, 16, 25, 30, and 31.

Insurance and protection module 335 provides information relating to some form of protection of goods or services purchased by a user. Such protection can be offered in the form of an insurance, purchase protection plan, extended warranty or insurance policy, or a combination thereof. In some scenarios, a purchase protection plan or policy can be offered by a user's financial institution or bank (e.g., an issuer of a financial instrument that is used to purchase the goods or services). In some embodiments, a warranty can be provided by one or more merchant, manufacturer, or retailer.

Figure 17:
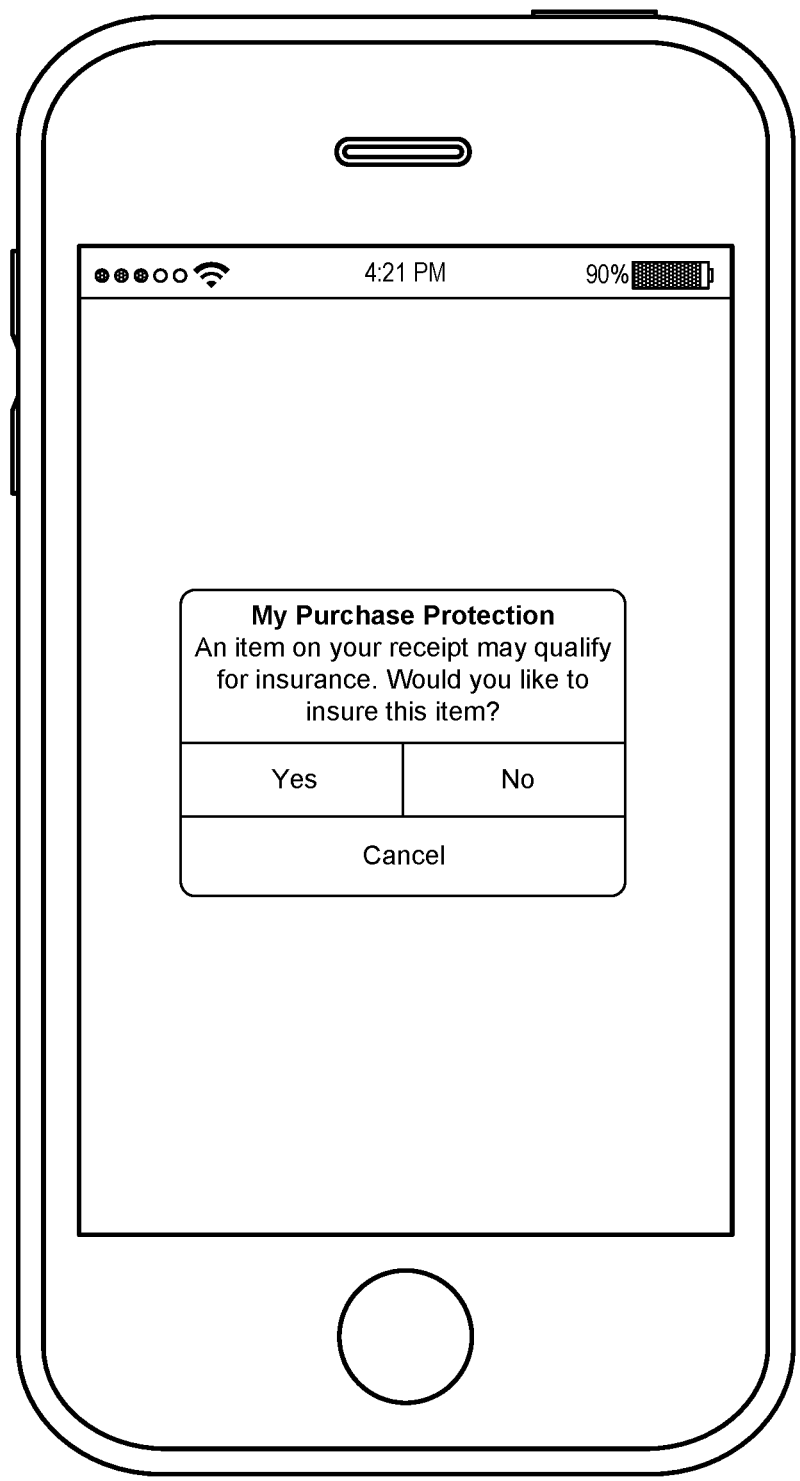

In some embodiments, an insurance provider provides an insurance policy that can cover goods or services purchased by a user, as shown in FIG. 17. Thus, according to embodiments of the present disclosure, insurance and protection module 335 can query an insurance provider, financial institution, or merchant to collect information about whether an insurance policy, purchase protection plan, and/or warranty (or a combination thereof) is applicable to the goods or services purchased by a user. Information relating to a user's purchases is typically received by receipt capture module 330, which then conveys the purchase information to insurance and protection module 335.

In an example, based on data from scanning a receipt, receipt capture module 330 can identify a financial instrument (e.g., a credit card number or a debit card number, either in whole or the last four digits) used in the purchase of goods or services, and an associated issuer of the financial instrument. The identification information of the financial instrument and the associated issuer can be communicated to insurance and protection module 335 for querying about potential purchase protection plans offered by the issuer that cover goods or services purchased by a user. Upon receiving a response from the issuer, insurance and protection module 335 can inform the user whether the protection plan covers the goods or services purchased.

In some embodiments, insurance and protection module 335 can aggregate a list of insurable items associated with the user, based on information provided by the user, and can recommend that the user buy protection plans for the insurable items. Thus, a user can list a television, water heater, air conditioner, one or more jewelry items, camera, home theater, couch, bed, watch, any type of electronic appliance, any type of furniture, or, in general, any form of goods or services. A user can provide (via a mobile application, desktop application, or other electronic methods) information pertaining to one or more items that are insurable. In some scenarios, receipt data manager platform 120 can monitor the list of insured items and send periodic reminders to a user in connection with routine maintenance of one or more items. For example, a reminder can be sent to a user to purchase filters for an air conditioner that is insured by the user.

Figure 18:
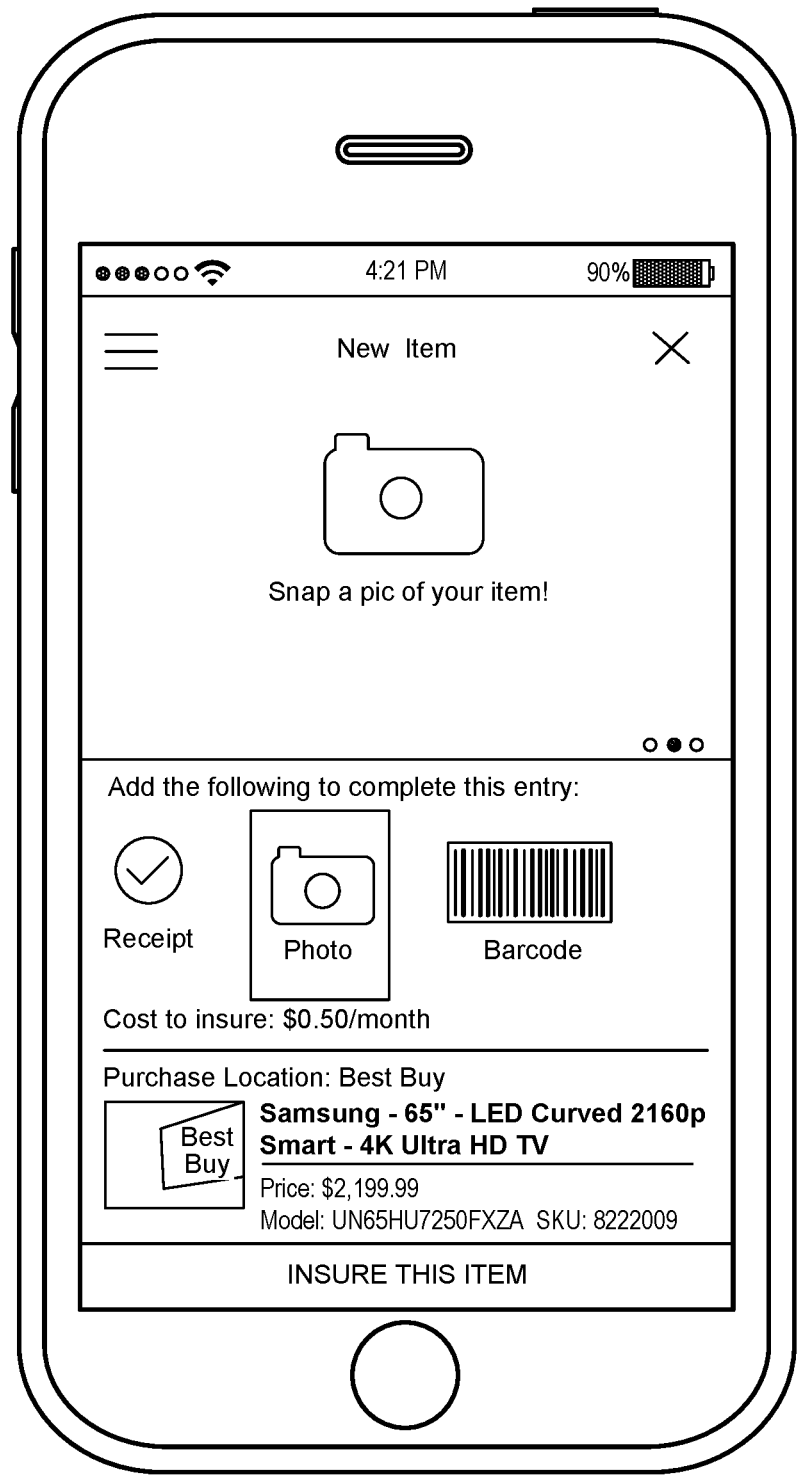
Figure 19:
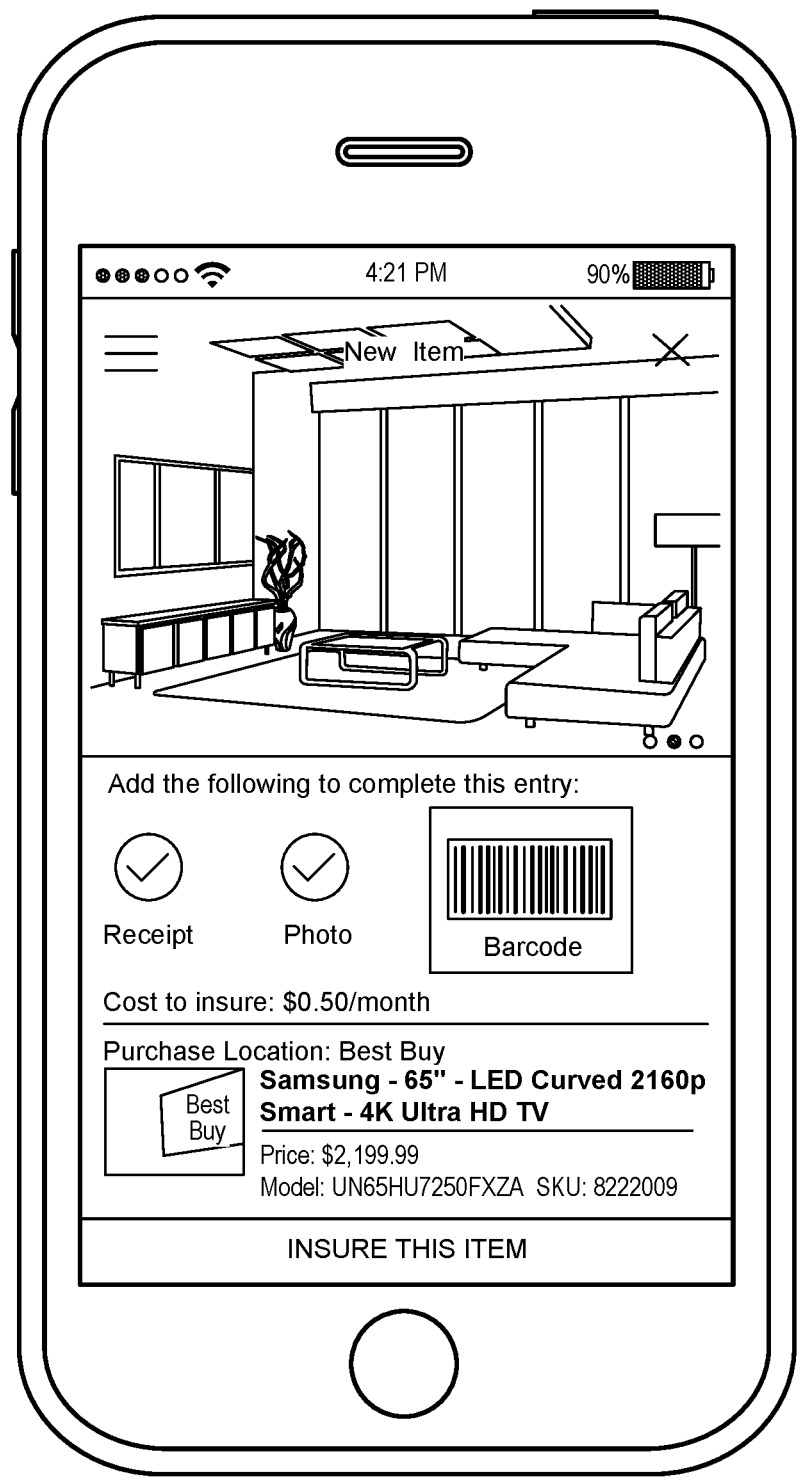
Figure 20:
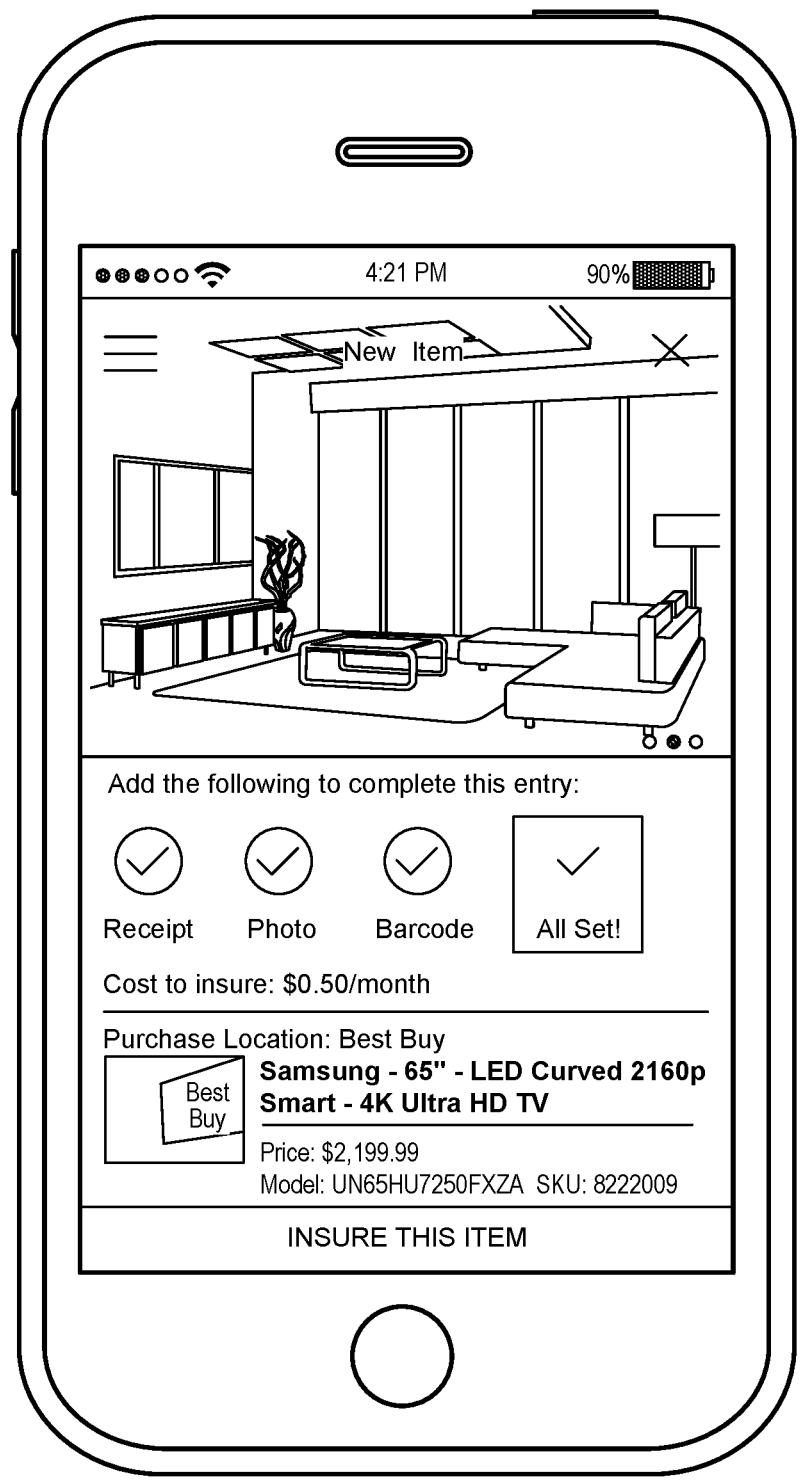
Figure 22:
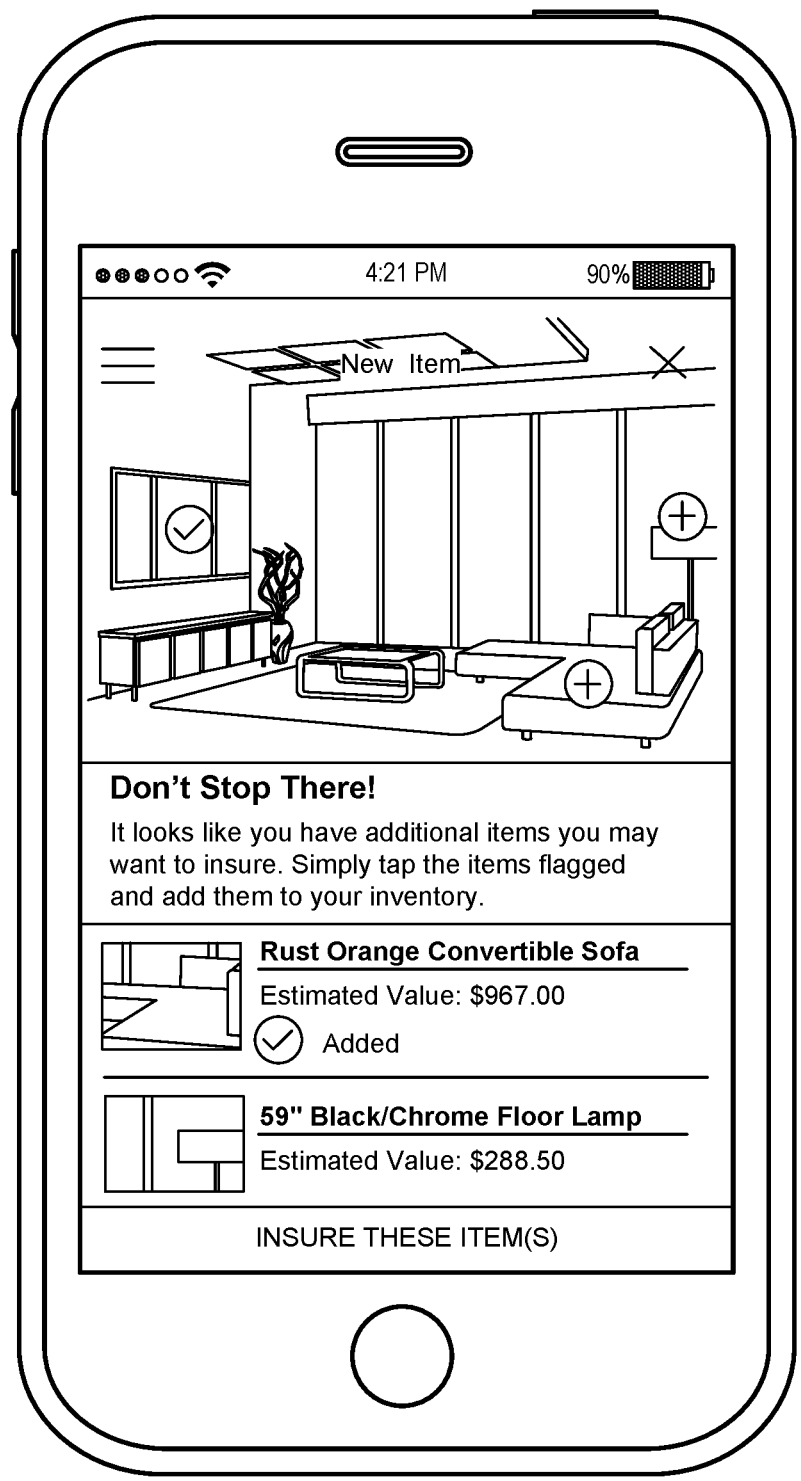
Figure 23:
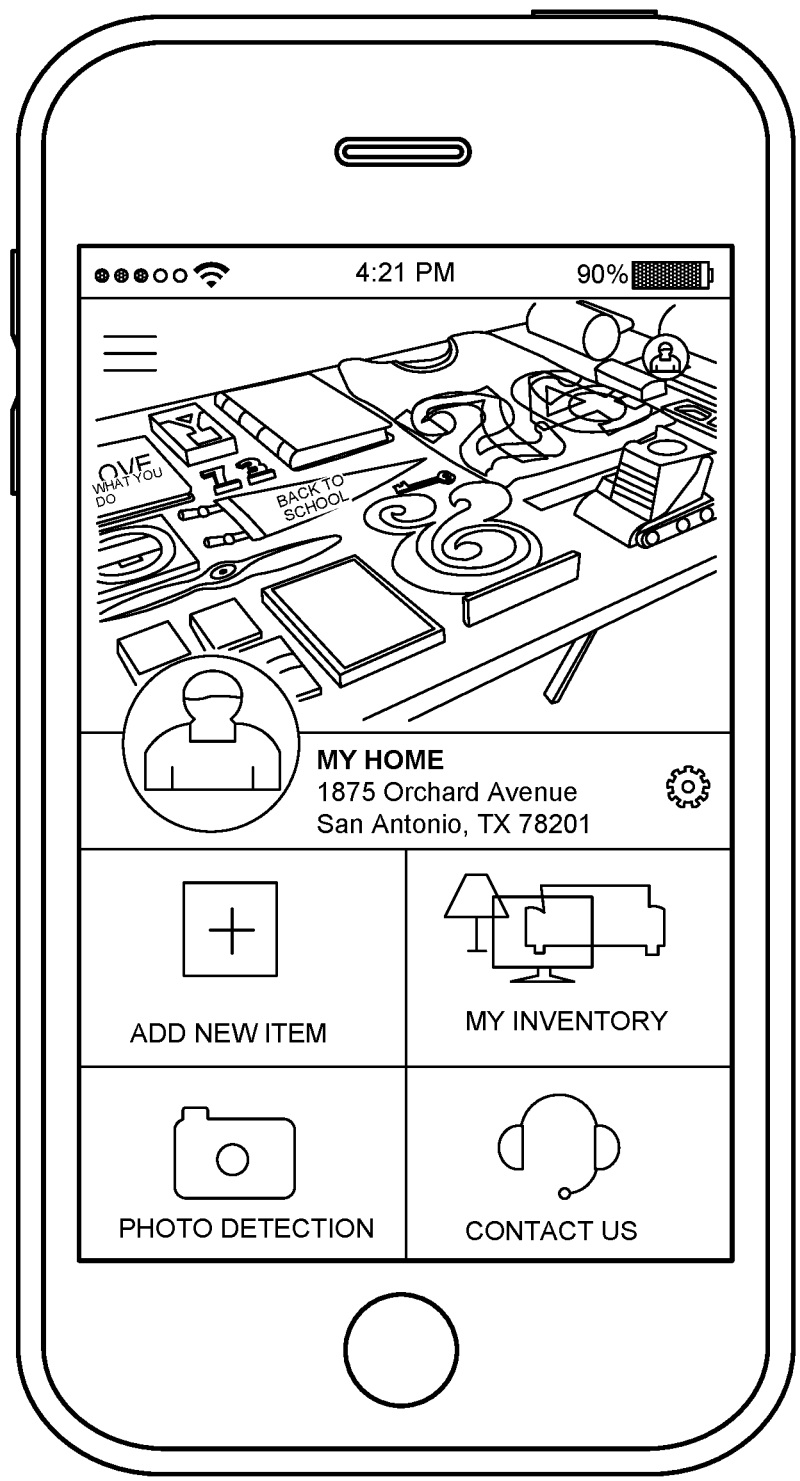
Figure 24:
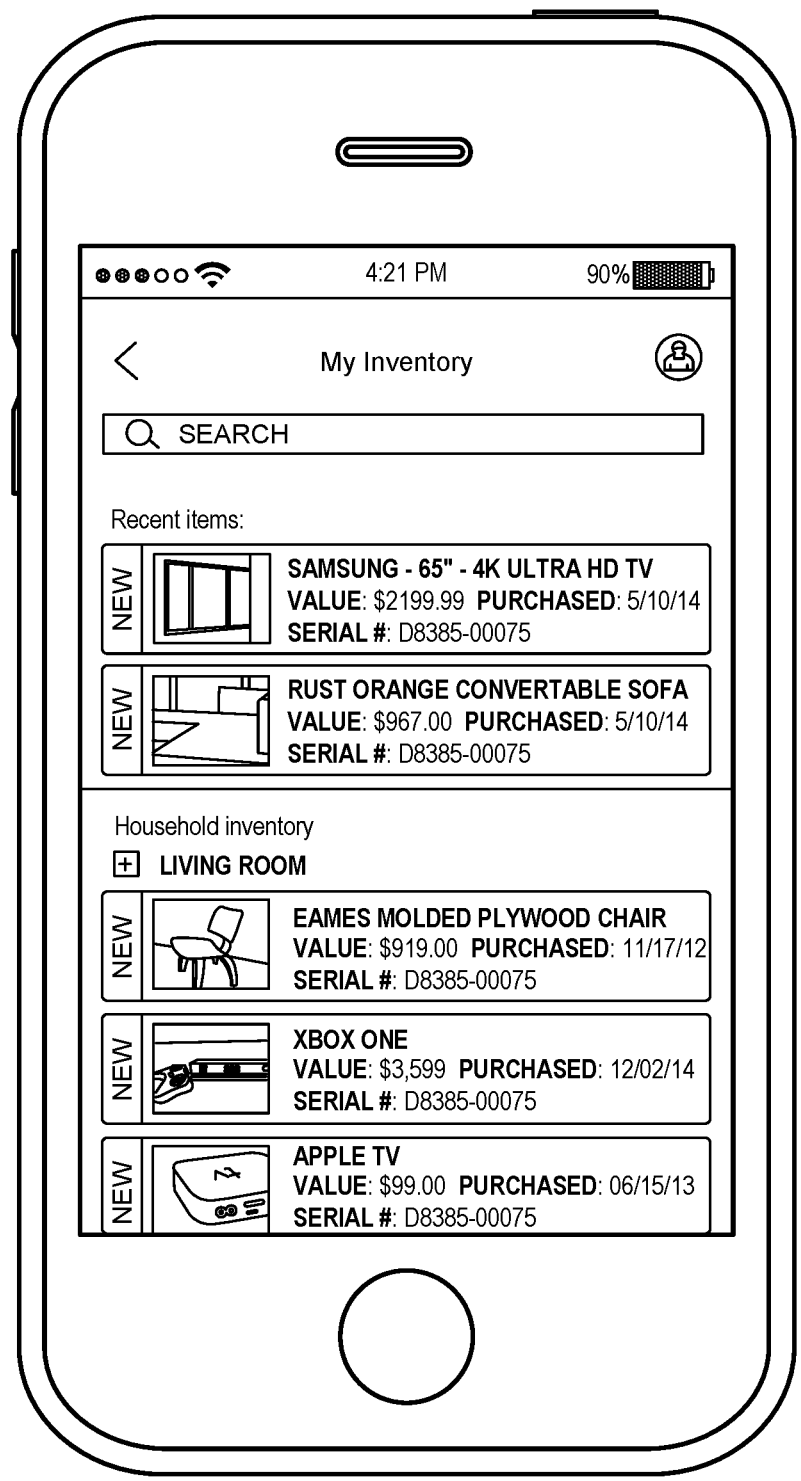

In some embodiments, insurance and protection module 335 can query the user for information relating to additional insurable items of goods or services, as shown in FIGS. 22, 23, and 24. In some embodiments, insurance and protection module 335 can detect that an insurance item was purchased (e.g., based on purchase price or brand) and can request a user to provide information relating to the first insurable item, such as a barcode, receipt, picture, radio frequency identification (RFID) tag, serial number, or detailed specification and model/brand number, as shown in FIGS. 17, 18, and 19. Upon the user submitting such information to receipt data manager platform 120 (FIG. 20), additional information (e.g., an image of the insurable goods or services in its operating environment such as a television installed in the user's living room) may be requested by the insurance and protection module 335. When the user takes an image of the goods or services and sends it to the receipt data manager platform 120, the insurance and protection module 335 can examine the image submitted by the user to identify other potential goods or services in the same operating environment (e.g., a home theater or a couch in the user's living room that may be insurable items) (FIG. 22 and FIG. 23). In some embodiments, the user can search for their insured items in a database (FIG. 24). Thus, embodiments of the present disclosure facilitate detection of additional insurable items of goods or services when information (e.g., an image) of a first insurable item of goods or services is submitted to the receipt data manager platform 120 (more specifically, the insurance and protection module 335 included therein).

In some embodiments, receipt data manager platform 120 can determine one or more insurable items of goods or services based on information in the purchase receipts. For example, based on information identifying (by receipt capture module 330) that a user has purchased filters for an air conditioner, receipt data manager platform 120 can determine that a user has an air conditioner. As another example, if receipt capture module 330 identifies a user has purchased a television stand based on receipt data of a furniture store, receipt data manager platform 120 can determine that a user has a television. In some embodiments, insurance and protection module 335 can query an insurance database to determine whether the insurable item of goods or services is covered under an existing insurance policy of the user. Upon determining that the insurable item of goods or services is not covered under the existing insurance policy of the user, insurance and protection module 335 can offer to the user a new insurance policy for the insurable item of goods or services.

Figure 21:
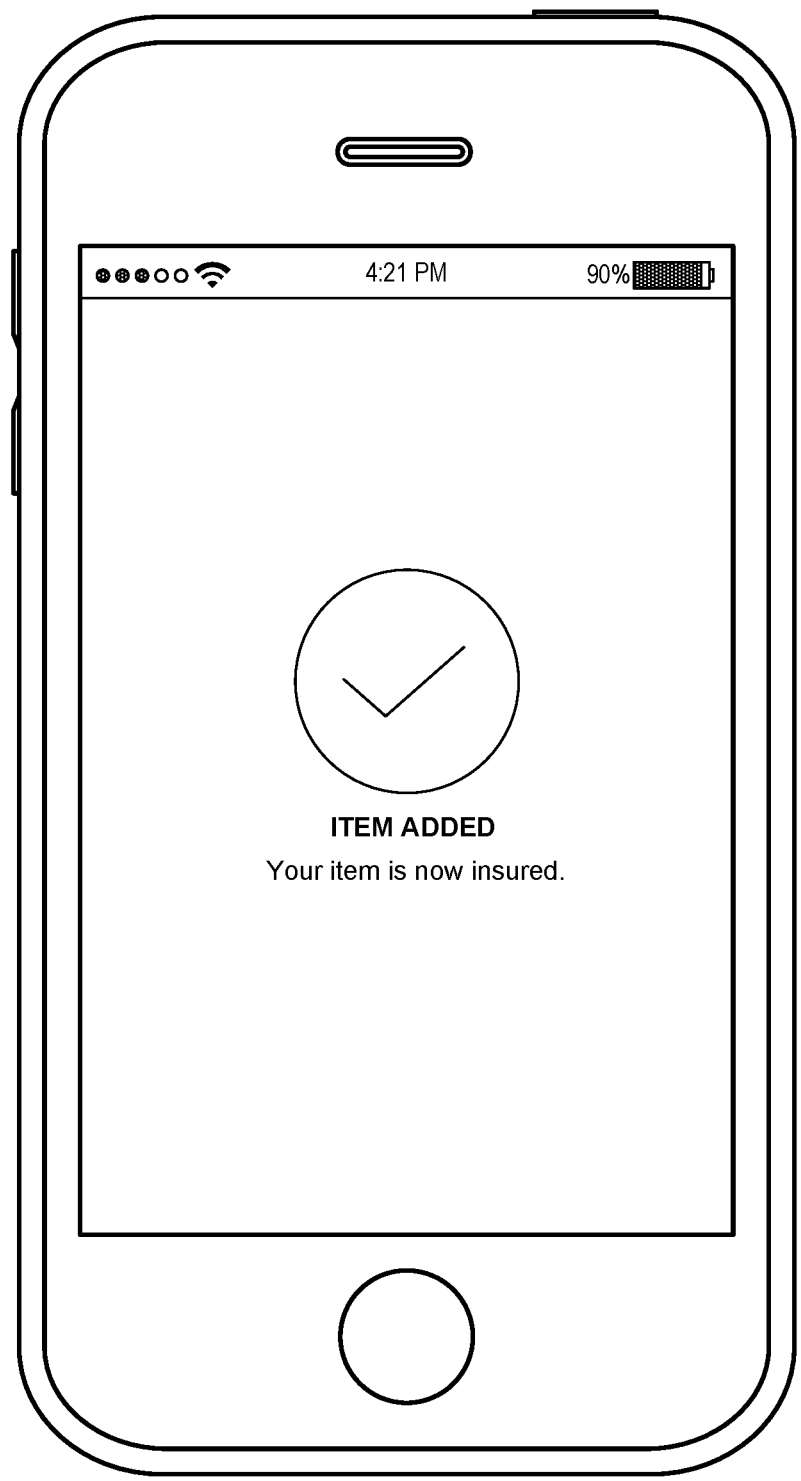

In some scenarios, an item is covered by an existing policy but has not been added to an insurance database (e.g., storing information of the insured items). Thus, in such scenarios, the insurance and protection module 335 can add the item into the profile of the user in the insurance database (FIG. 21). For example, a user can have a renter's insurance policy that covers all appliances, including a water heater. A user might have a water heater that is not yet added to the list of insured items. Thus, upon insurance and protection module 335 identifying that a user has a water heater that is covered by the user's policy but has not yet been added to a database storing information of the insured items, insurance and protection module 335 can update the profile of the user in the database to include the water heater.

Figure 12:
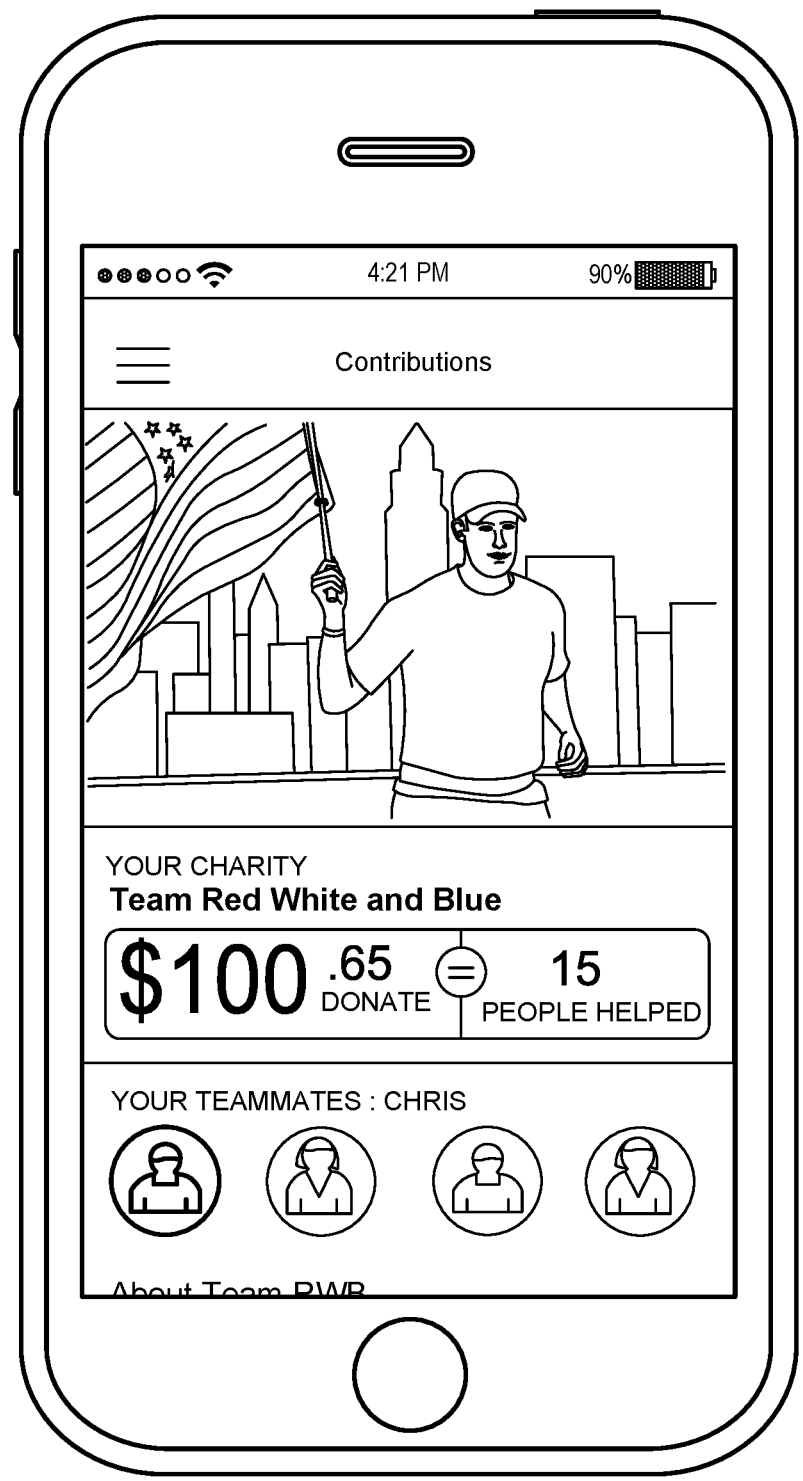
Figure 13:
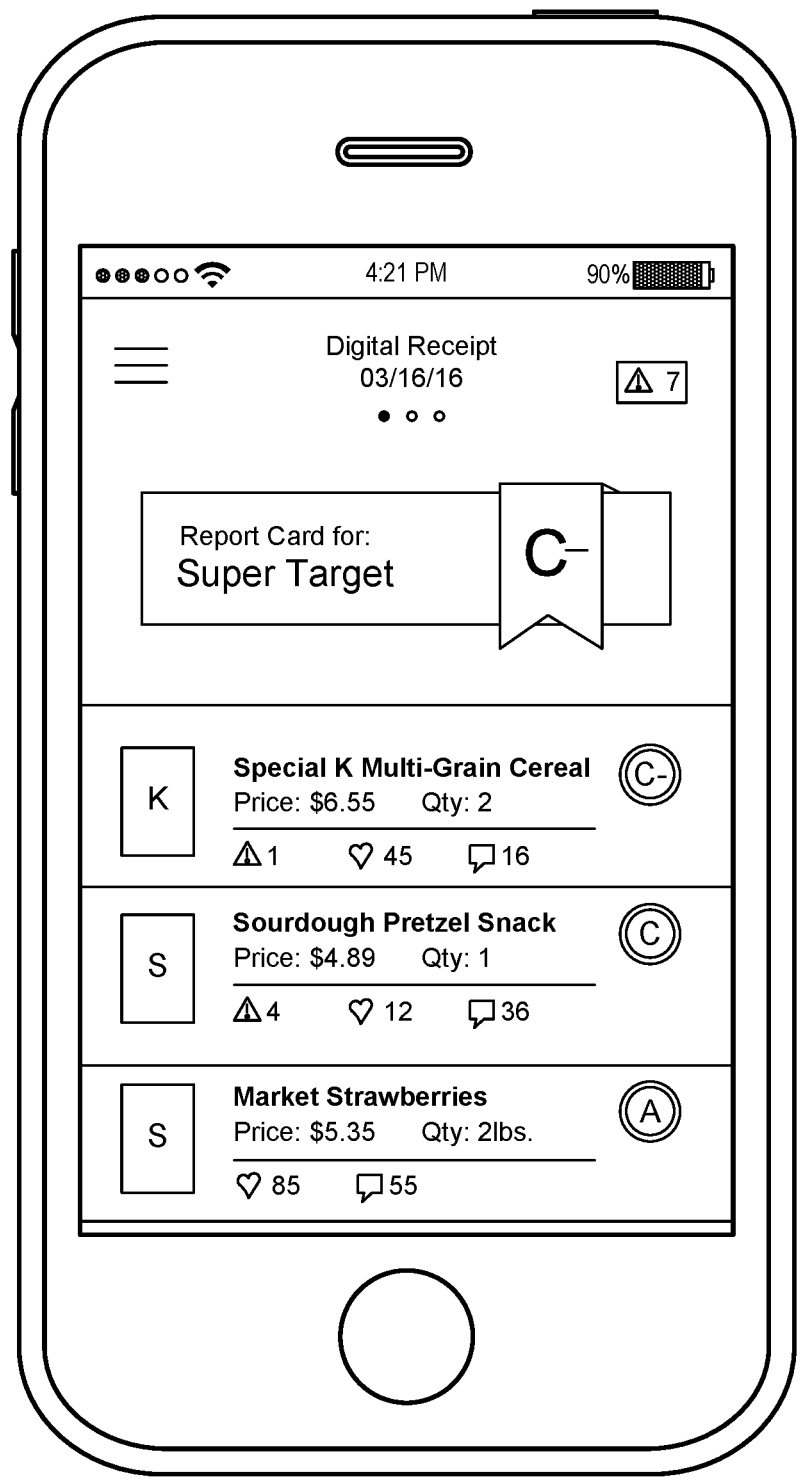

Charitable giving module 340 manages user donations to one or more charities of a user's choice, based on purchase information in receipts, as provided by receipt capture module 330. Charitable giving module 340 communicates with the receipt capture module 330 for obtaining receipt data that can be used in determining a value of charitable contribution. Charitable giving module 340 stores names and information of such charities, value contributed by a user, date of contribution, and the like. In some instances, charitable giving module 340 gamifies a user's charitable contribution. For example, a spinning wheel can be displayed with which a user can interact, via a GUI, on a user's mobile device or computing device. The user can spin the wheel and choose to contribute to a charity based on a percentage of one or more receipts, or, based on the amount displayed on the wheel, as shown in FIG. 11. The one or more receipts that determine the user's charitable contributions can be selected by either a user, the receipt data manager platform 120, or both. In some embodiments, a user can share on a social media network information relating to the charitable contributions. In some instances, multiple users can sign up as a team for contributing to a charity, based on common interests, social causes, and/or preferences, as shown in FIG. 12. The charitable giving module 340 can query the profile module 315 to determine a user's preferences.

Figure 25:
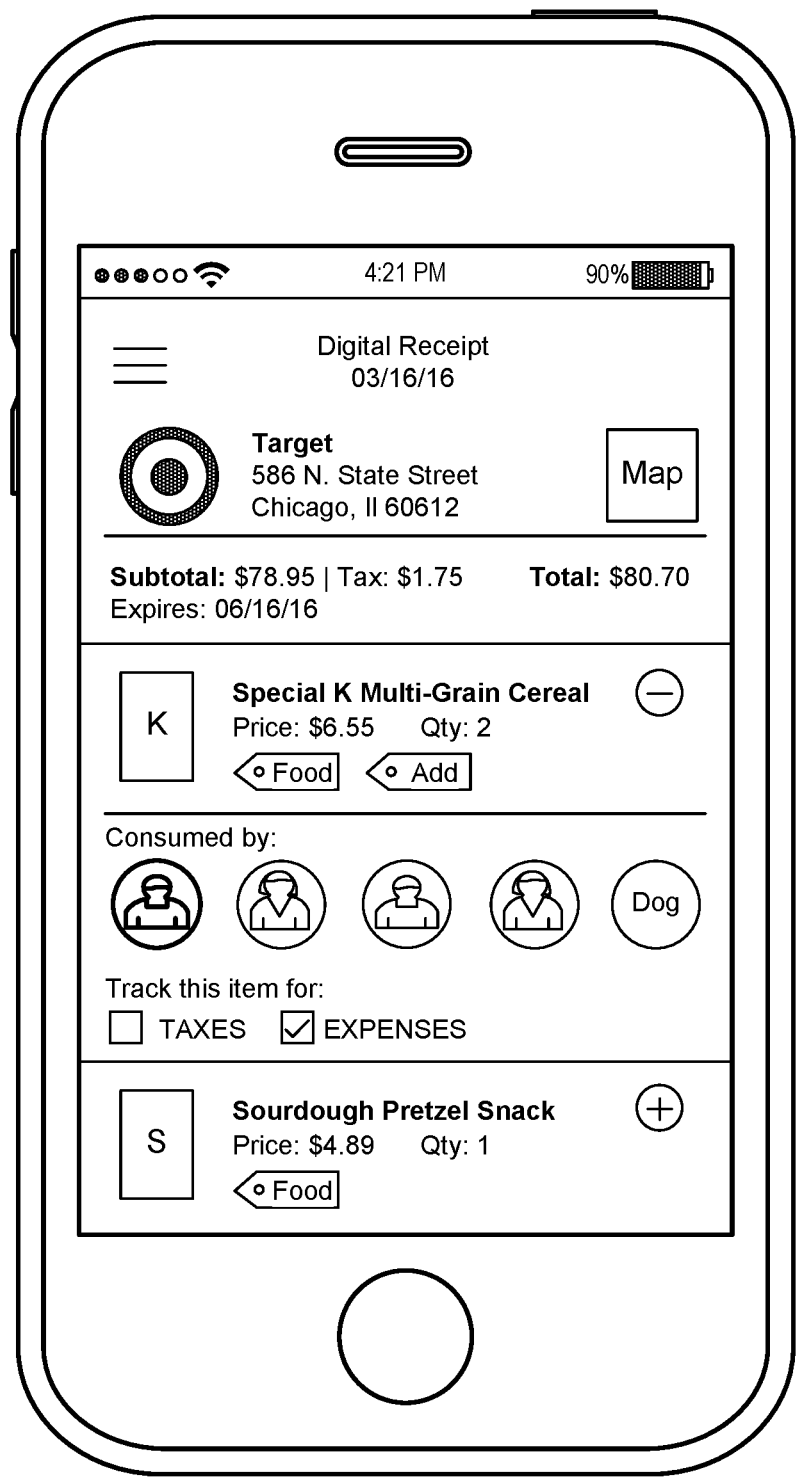
Figure 26:
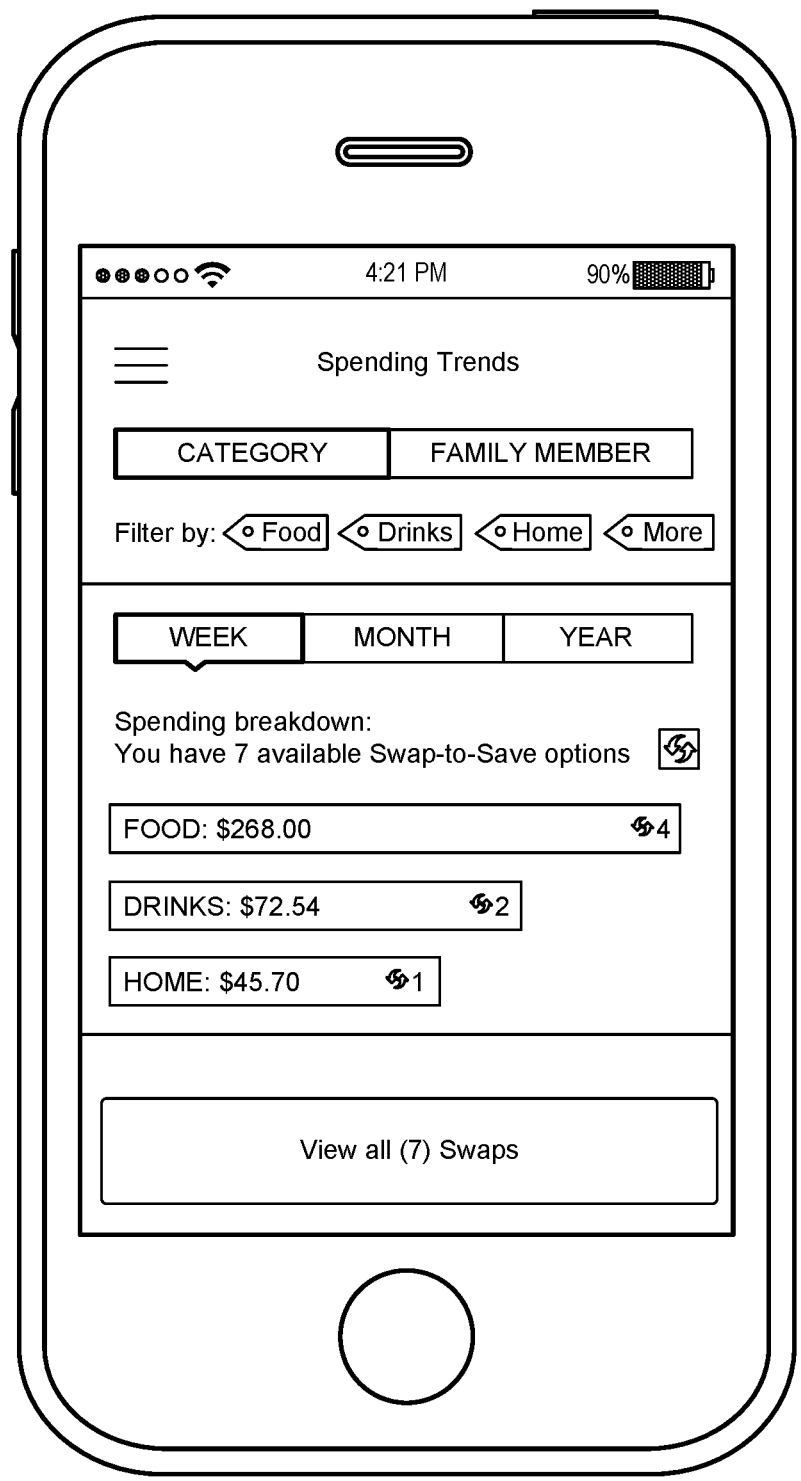
Figure 30:
Figure 31:
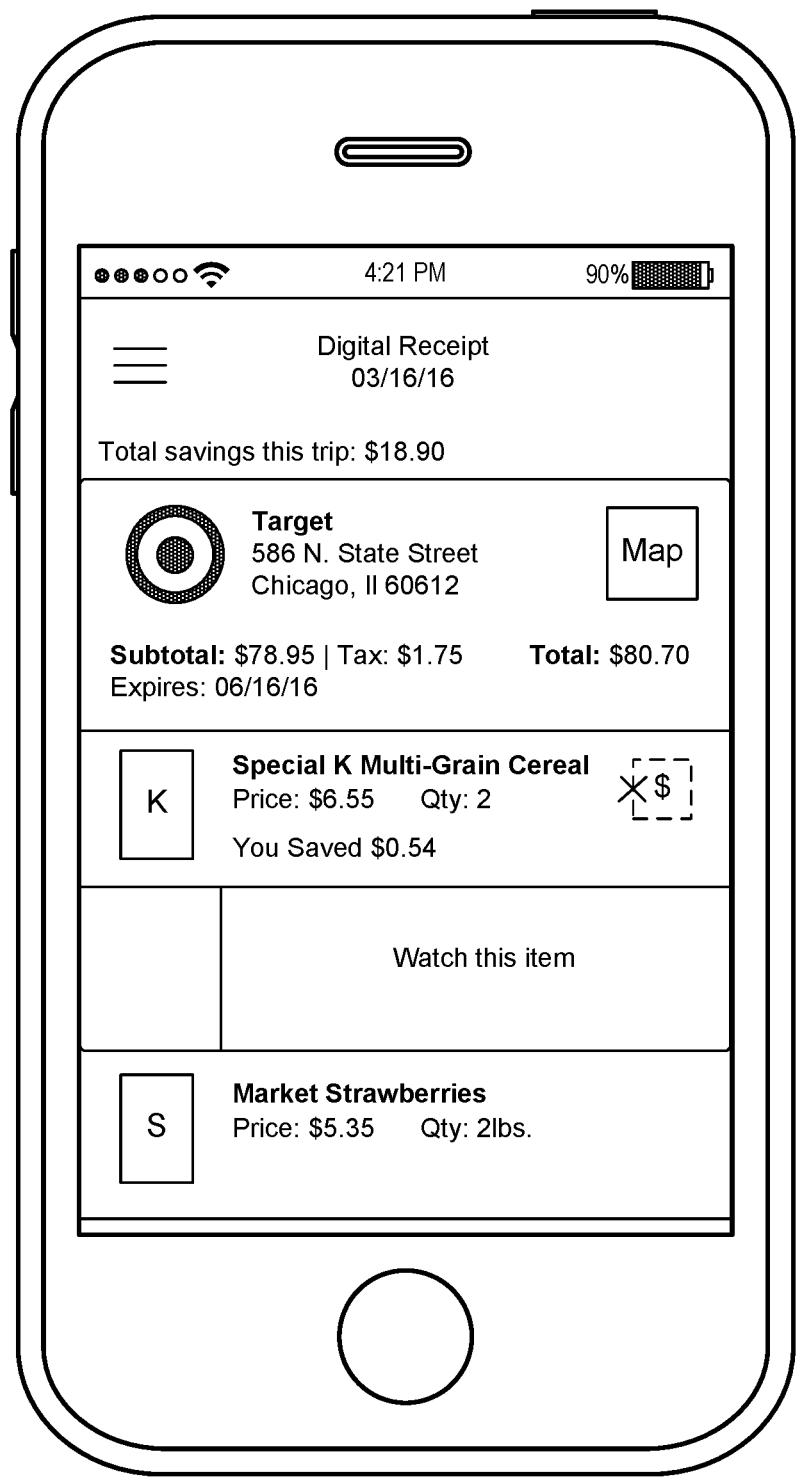

Savings and budgeting module 345 can determine options for savings for goods or services purchased by a user, and tracking a budget tailored for the user. In some embodiments, as shown in FIGS. 30 and 31, savings and budgeting module 345 can determine an amount saved by a user in purchases of goods or services at a merchant. In some embodiments, savings and budgeting module 345 can determine a user's spending trends (e.g., how much money a user has spent on a certain category or subcategory of goods or services relative to a target spending limit (during weekly, monthly, quarterly, semi-annually, annually, or other time periods) in categories and subcategories that are pre-determined by the user. FIG. 25 illustrate spending trends in various categories.

Figure 27:
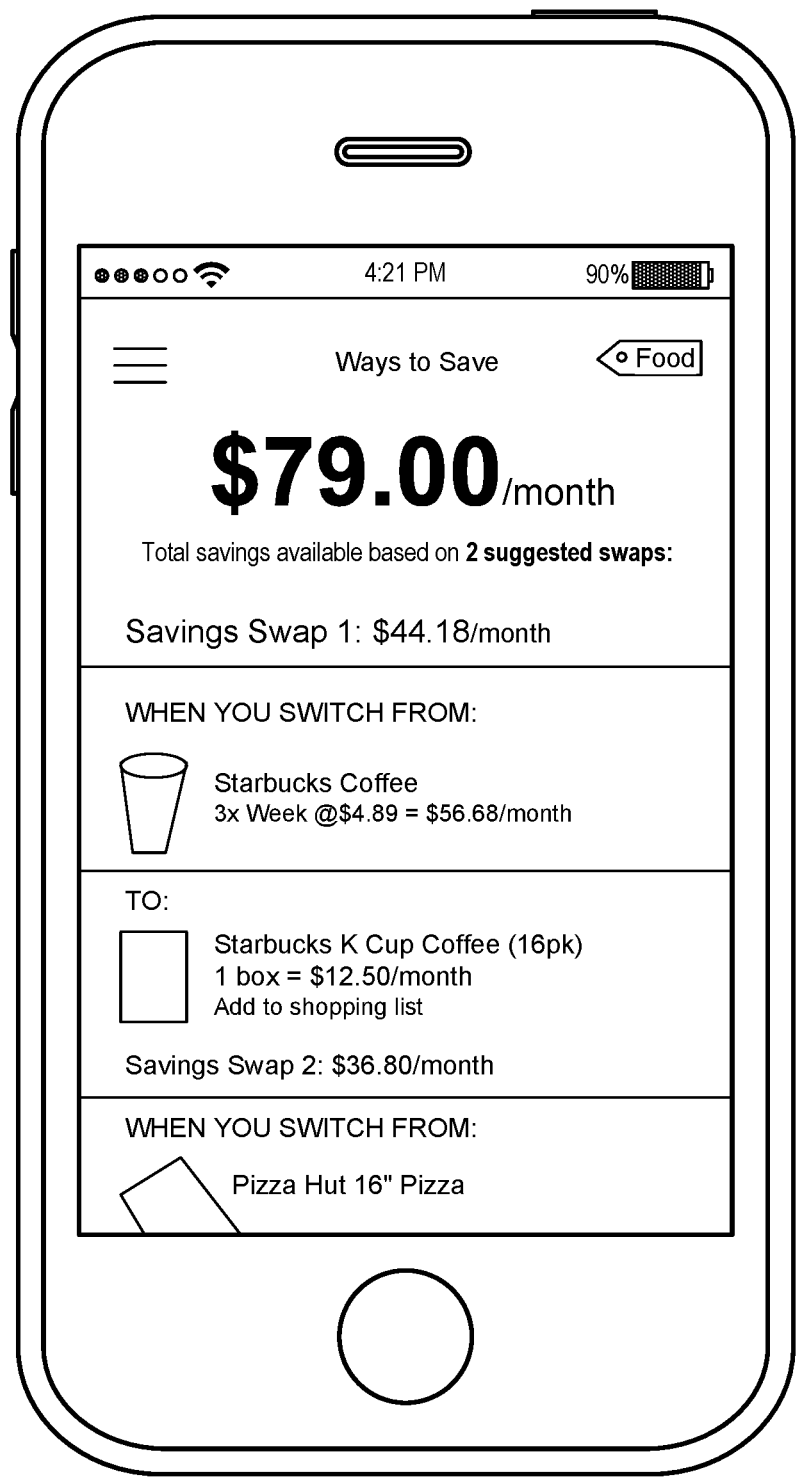
Figure 28:
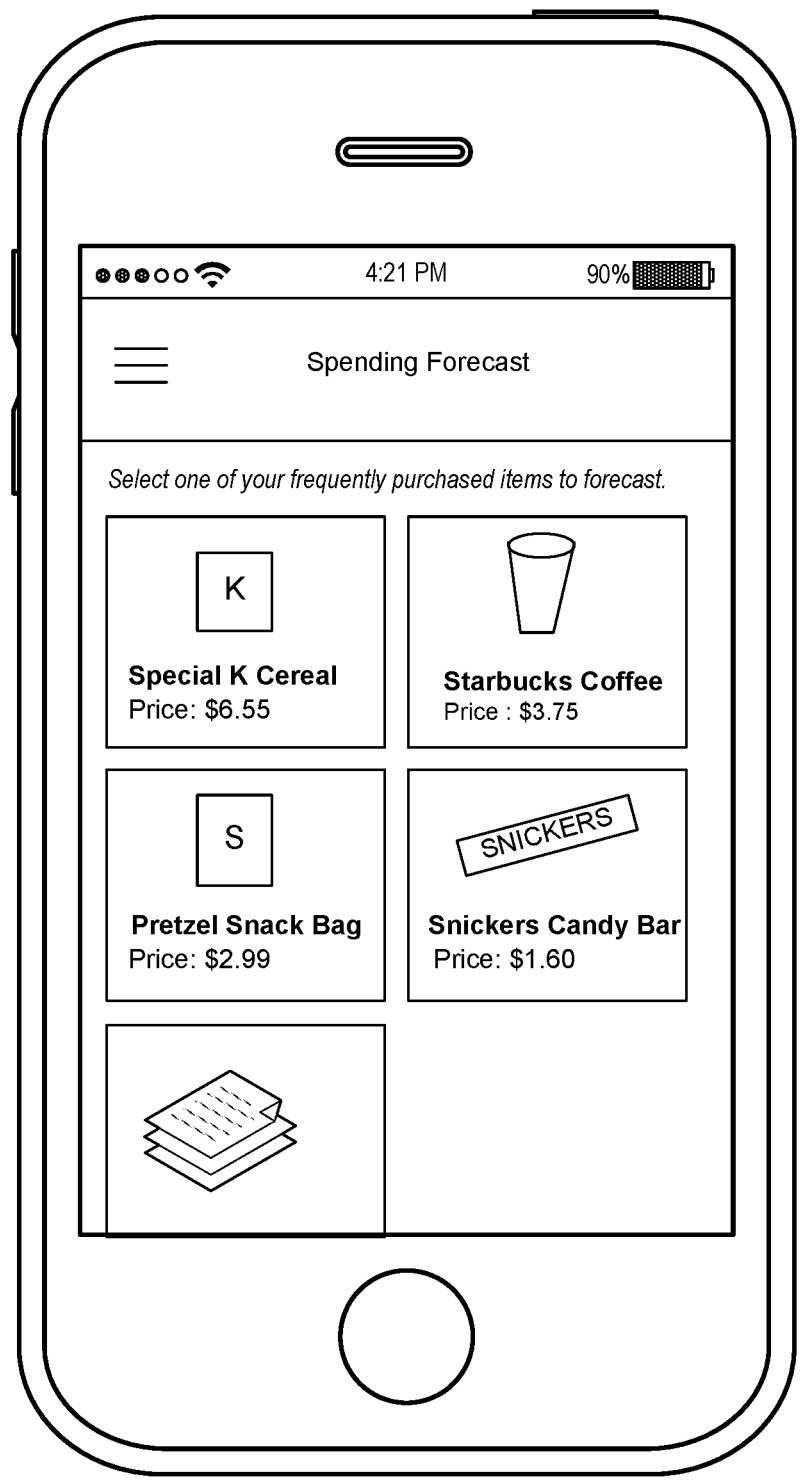
Figure 29:

In some scenarios, as shown in FIG. 27, savings and budgeting module 345 can recommend alternate options in which a user can save money, such as alternate goods or services that can be lower-priced, of better quality, or both. In some embodiments, savings and budgeting module 345 can use predictive analytics to forecast how much money a user is going to spend in the future, based on the user's historical purchase habits. Such forecast can be directed at specific goods or services, or specific categories or subcategories of interest to a user, as shown in FIGS. 28 and 29. A user can interact with the savings and budgeting module 345 by a mobile application or a desktop application, and can indicate his or her preferences that are factored in the forecast by the receipt data manager platform 120. In some embodiments, the spending data can be aggregated for a group of users to determine trends. For example, the service provider can determine that a group of users are each having the same life event (e.g., having a baby) and negotiate with manufacturers based on the life event (e.g., car seat manufacturer). In some embodiments, data regarding a particular group of users (e.g., age, sex, race) can be aggregated and sold to third parties.

Figure 32:
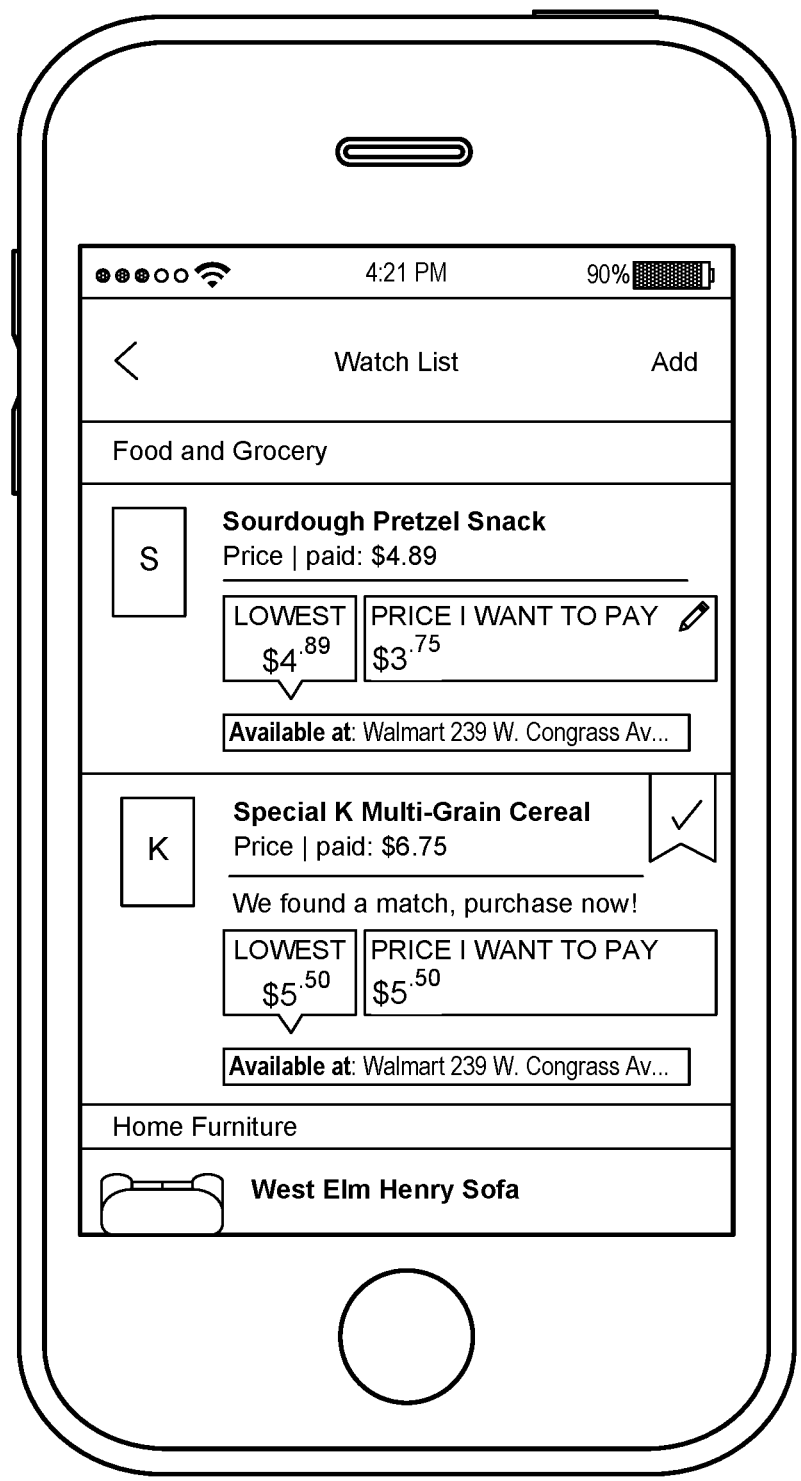
Figure 33:
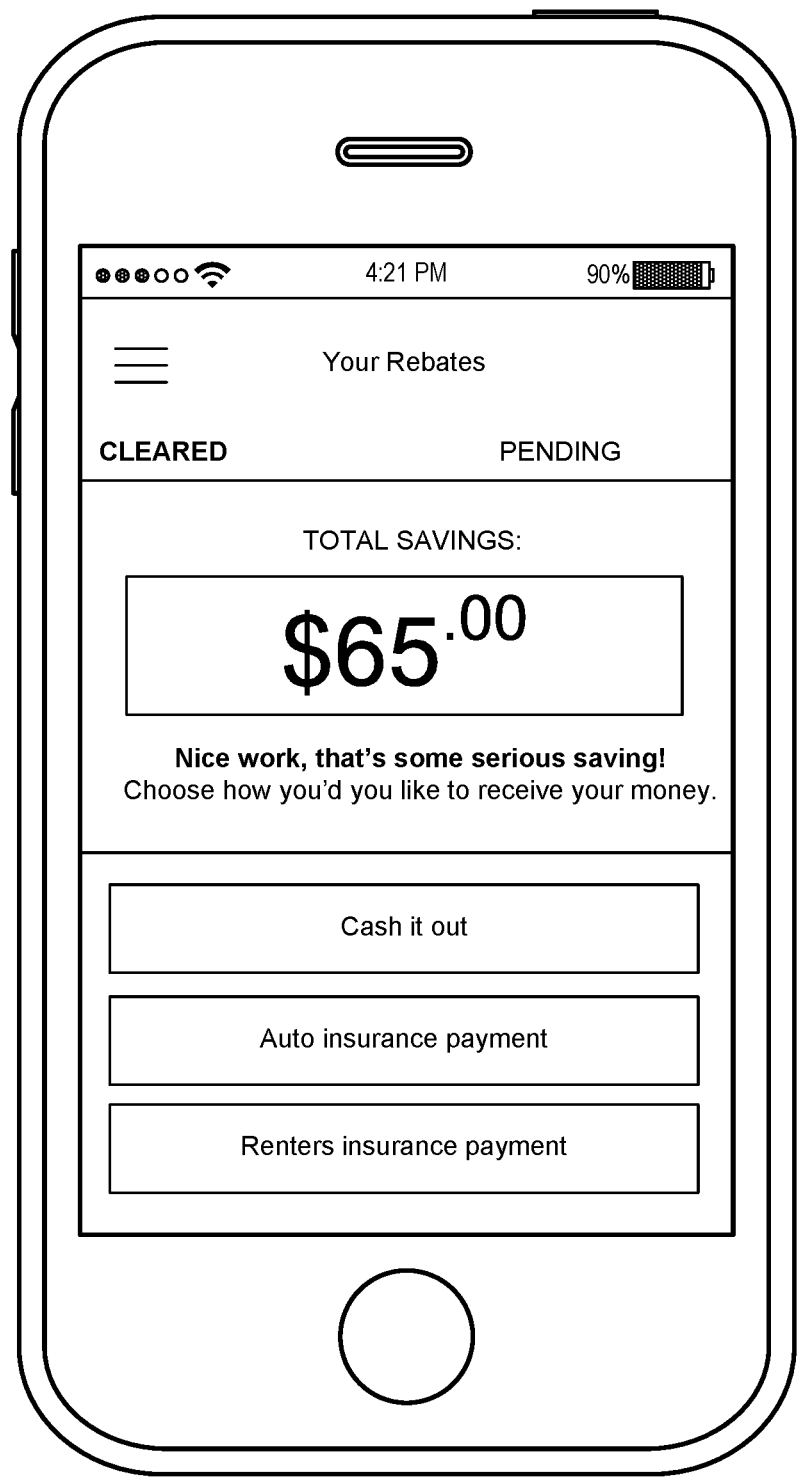

In some instances, savings and budgeting module 345 can determine the user's frequently used goods or services and provide spending forecasts for the frequently used goods or services. In some embodiments, as shown in FIG. 32, savings and budgeting module 345 can provide the ability to track price changes for goods and purchases purchased by a user (e.g., as indicated by information from receipt capture module 330). Moreover, savings and budgeting module 345 can also provide information relating to best times (e.g., optimized according to demand/supply cycles in the market and other market factors) to purchase certain goods or services of interest to the user, as well as associated merchant locations. The information provided by savings and budgeting module 345 can include a recommendation to switch from a physical store to an online retailer so that the user can save money. In some embodiments, savings and budgeting module 345 can provide coupons, rebates, and other incentives to a user for certain goods or services. This provides the option to save money by switching to an alternate brand. In some embodiments, the savings can be cashed out by a user (e.g., as a check). In some embodiments, a user can choose to transfer his or her savings towards payment of insurance premiums, as shown in FIG. 32. In some scenarios, savings and budgeting module 345 can order, from one or more merchants, various items of goods or services, on behalf of the user. For example, by historically analyzing the frequency of purchases of regularly used household items, savings and budgeting module 345 can create a list of such items, request the user for his or her consent to place the order, and then order such items from an online retailer using the credit/debit card information stored in profile module 315.

FIGS. 4-7 are flowcharts illustrating sets of operations for capturing, managing, and using receipt data. In some embodiments, fewer than all of the operations in each set of operations are performed, whereas, in other embodiments, additional operations are performed. Moreover, in some embodiments, the operations may be performed in different sequences or in parallel. The operations in FIGS. 4-7 are performed by a server (e.g., receipt data manager platform 120) illustrated in FIG. 3. In some embodiments, the device 200 performs one or more of the operations in FIGS. 4-7.

Figure 4:
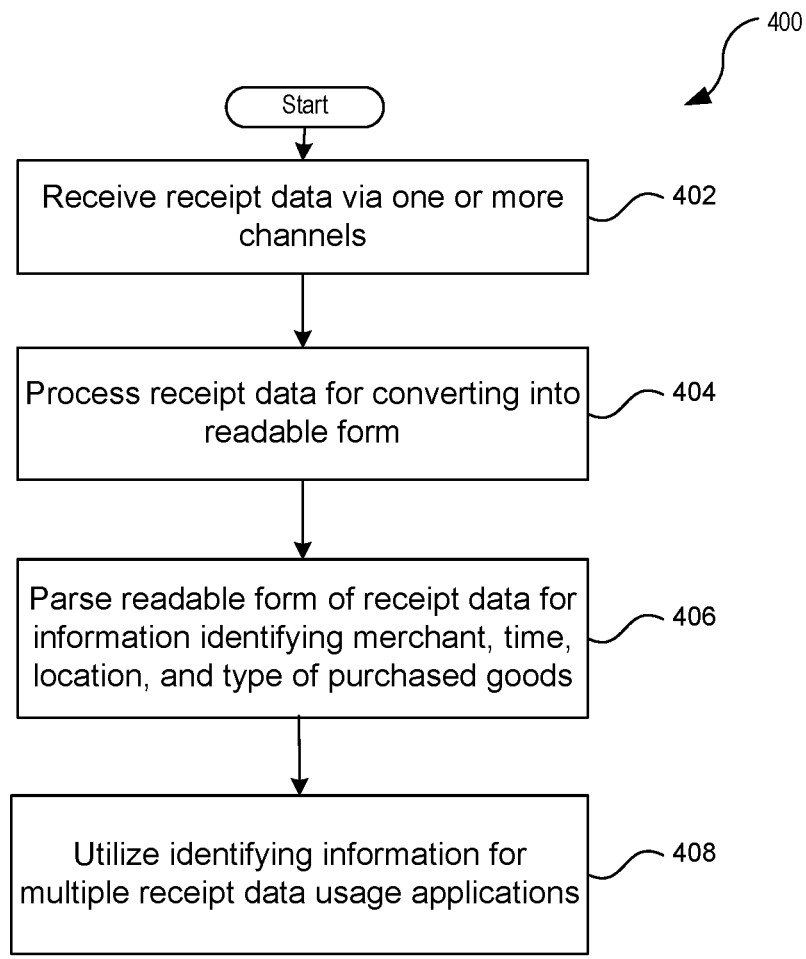
FIG. 4 is a flowchart illustrating a set of operations for receipt data use from the perspective of a user's mobile device, in accordance with various embodiments of the disclosure.

FIG. 4 is a flowchart illustrating a set of operations 400 for capturing receipt data, in which the operations are being performed by a server. Receiving operation 402 receives receipt data via one or more channels. Examples of channels can be a short message service (SMS) message, a multimedia message service (MMS) message, or an email message. A receipt can be sent electronically to receipt data manager platform 120 by a user or by a merchant associated with the purchased goods or services, or by both the user and the merchant.

Processing operation 404 processes receipt data for converting the receipt data into a readable form. This can include optical character recognition or other methodologies for scanning electronic receipts and converting them into readable form. Parsing operation 406 parses the readable form of the receipt data for identifying information included in the receipt. Examples of such information can include a merchant name, one or more items of goods or services, time of purchase, location of purchase (or merchant location), an address, phone number, email address, type of purchased goods or services, and the price of one or more items purchased. Utilizing operation 408 utilizes the information identified in the receipt in multiple receipt data use applications. Examples of such applications are (without limitation) generating customized recommendations for healthier items of consumable goods or services (e.g., food or beverage), determining insurable items from receipt line item data, creating forecasts geared toward budgeting and saving, facilitating donations to charities based on a percentage of the price of one or more items in receipt line data, and other applications that utilize receipt data.

Figure 5:
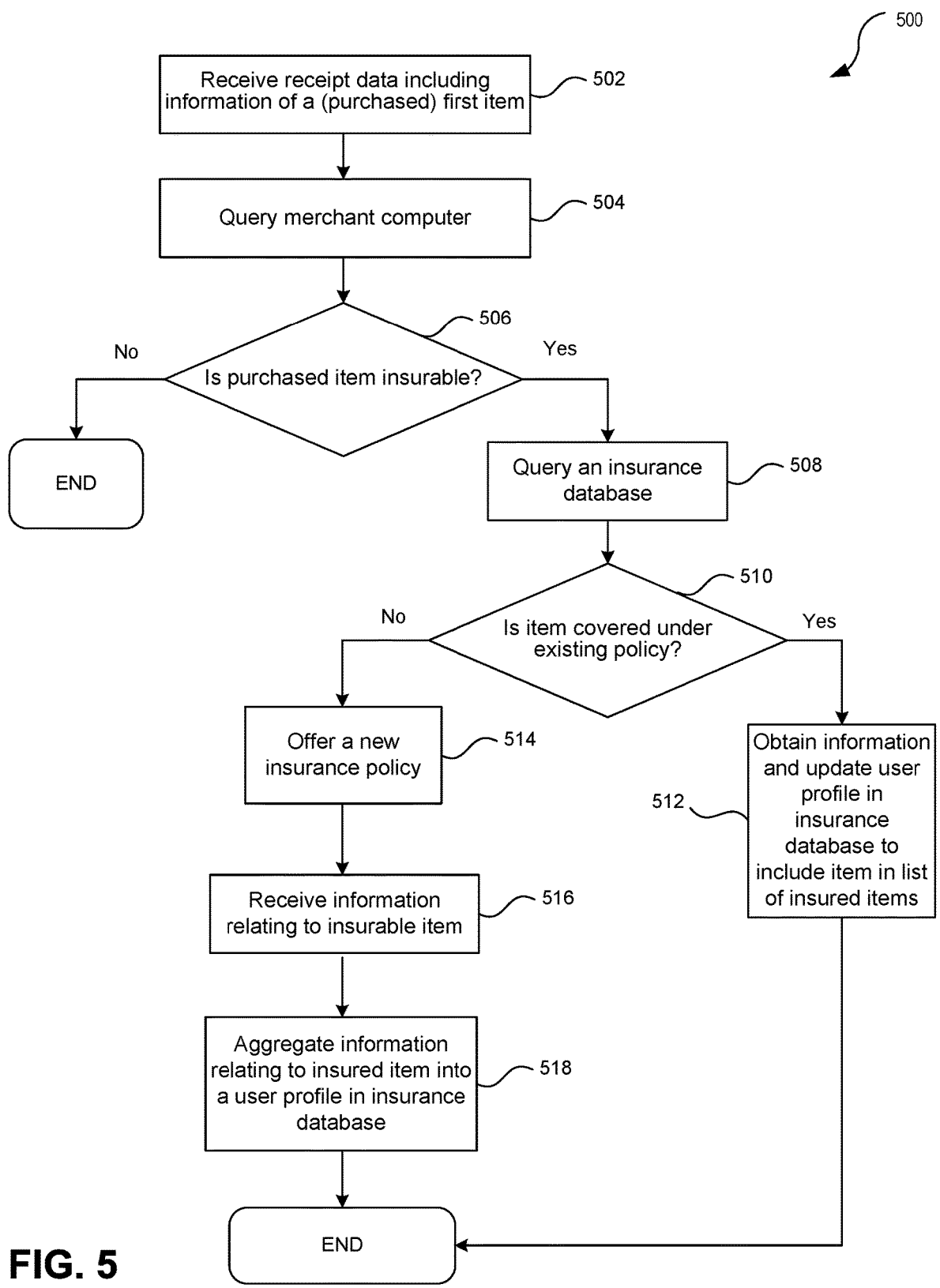
FIG. 5 is a flowchart illustrating a set of operations for receipt data use from the perspective of a server, in accordance with various embodiments of the disclosure.

FIG. 5 is a flowchart illustrating a set of operations 500 for aggregating into an insurance database the insurable items contained in a user profile. Receive operation 502 receives receipt data, which includes the price, description, UPC or other product identification code, of one or more items of goods or services purchased by a user. Receipt data can also include a merchant name, one or more items of goods or services, the time of purchase, the location of purchase (or, merchant location), an address, phone number, email address, the type of purchased goods or services, and the like. Querying operation 504 queries a merchant computer based on the description, UPC or other product identification code, or price of the one or more items of goods or services purchased by the user. Decision operation 506 determines whether the one or more items purchased by the user are insurable items of goods or services. When the decision operation determines that the item is not an insurable item, the process terminates. However, when the decision operation determines that the item is an insurable item, then querying operation 508 is invoked. Querying operation 508 queries an insurance database. Decision operation 510 determines whether or not the insurable item is covered by an existing insurance policy of the user. When the decision operation 510 determines that the insurable item is covered by an existing insurance policy of the user, but, for example, the insurable item has not been added to the user's policy profile, then updating operation 512 is invoked. Updating operation 512 obtains information relating to the item and updates the user's profile in the insurance database to include the purchased item in a list of insured items. If the decision operation 510 determines that the insurable item is not covered by an existing insurance policy of the user, offering operation 514 is invoked.

Offering operation 514 offers a new insurance policy to the user that covers the purchased item. Receiving operation 516 receives information relating to the insurable item (i.e., the purchased item) from a user. Thus, a user, for example, can provide such information in the form of a radio frequency identification (RFID) tag, a barcode, and/or a serial number. Aggregating operation 518 aggregates the user-provided information relating to the insured item into the user's profile in the insurance database. The process terminates thereafter.

Figure 6:
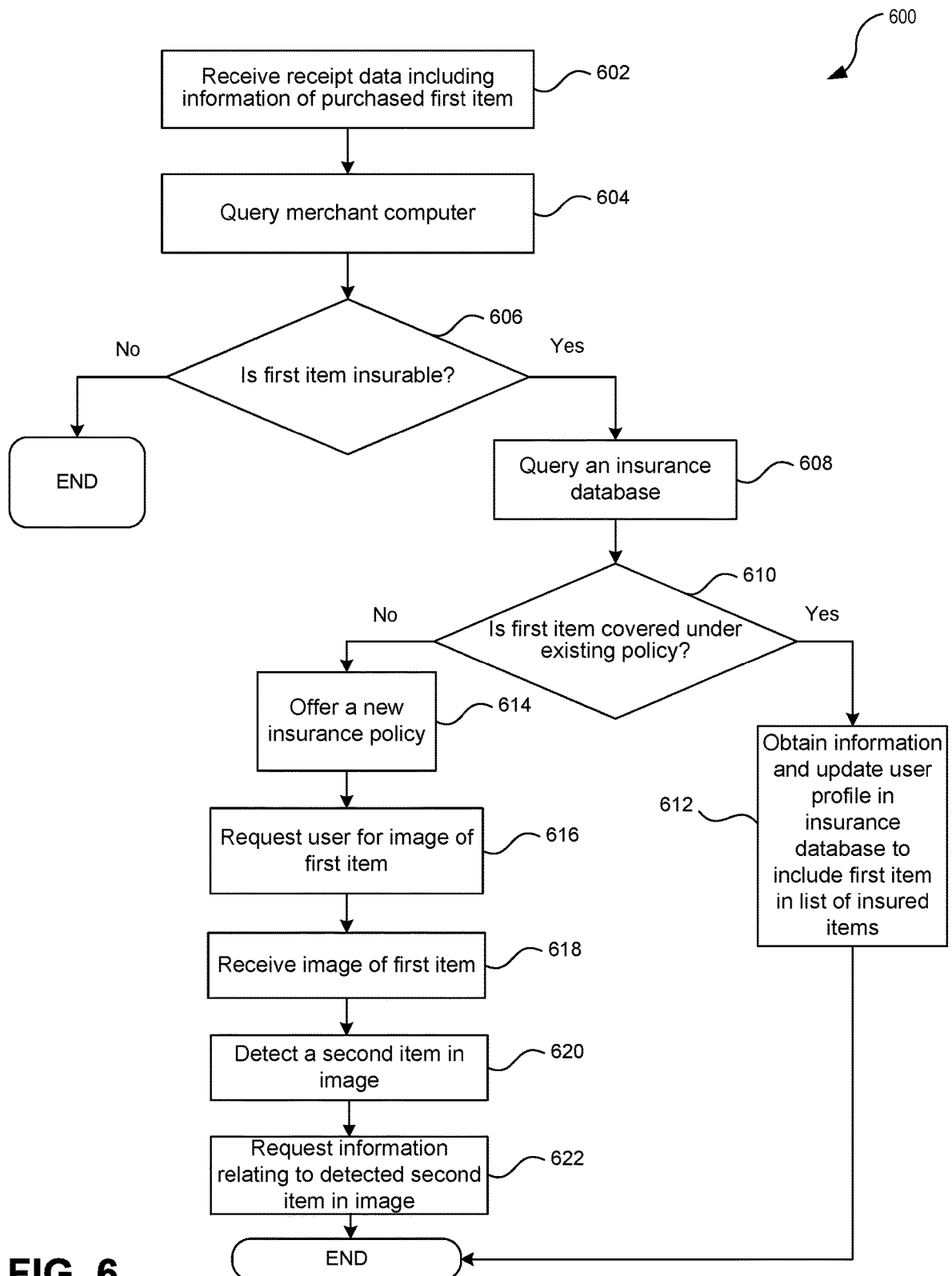
FIG. 6 is a flowchart illustrating a set of operations for receipt data use from the perspective of a server, in accordance with various embodiments of the disclosure.

FIG. 6 is a flowchart illustrating a set of operations 600 for detecting insurable items based on scanning images. Receive operation 602 receives receipt data, which includes the price of a first item of goods or services purchased by a user. Receipt data can also include a merchant name, one or more items of goods or services, a time of purchase, a location of purchase (or merchant location), an address, phone number, email address, a type of purchased goods or services, and the like. Querying operation 604 queries a merchant computer based on the price of the purchased first item of goods or services. Decision operation 606 determines whether the first item purchased by the user is an insurable item of goods or services. When the decision operation determines that the first item is not an insurable item, then the process terminates. However, when the decision operation determines that the first item is an insurable item, then querying operation 608 is invoked. Querying operation 608 queries an insurance database. Decision operation 610 determines whether or not the first item is covered by an existing insurance policy of the user. When the decision operation 610 determines that the first item is covered by an existing insurance policy of the user, but, for example, the first item has not been added to the user's policy profile, then updating operation 612 is invoked. Updating operation 612 obtains information about the purchase from the user and updates the user's profile in the insurance database to include the purchased first item in a list of insured items. If the decision operation 610 determines that the first item is not covered by an existing insurance policy of the user, offering operation 614 is invoked. Offering operation 614 offers a new insurance policy to the user that covers the purchased first item. Requesting operation 616 requests from a user an image of a first item. A user can take an image of the first item which shows the position it occupies in the operating environment (e.g., a television in a user's living room) and communicate the image to the receipt data manager platform 120. The image can be sent via a mobile application running on the user's mobile device, where the mobile application is associated with the receipt data manager platform 120. In some scenarios, a user can upload the image of the first item via a desktop application, send it as an email attachment, or send it as a text/multimedia message.

Receiving operation 618 receives the image of the first item sent by the user. Detection operation 620 detects a second item in the image of the first item. For example, if the first item is a television in a user's living room, a second item in an image of the first item can be a home theater, external speakers, TV stand, lamp, couch, rug, or any other item that is included in the image of the first item. Requesting operation 622 requests information relating to the second item, from the user. This information can, for example, be used to determine whether the second item is insurable, and, accordingly, can added to the user's policy profile in an insurance database.

Figure 7:
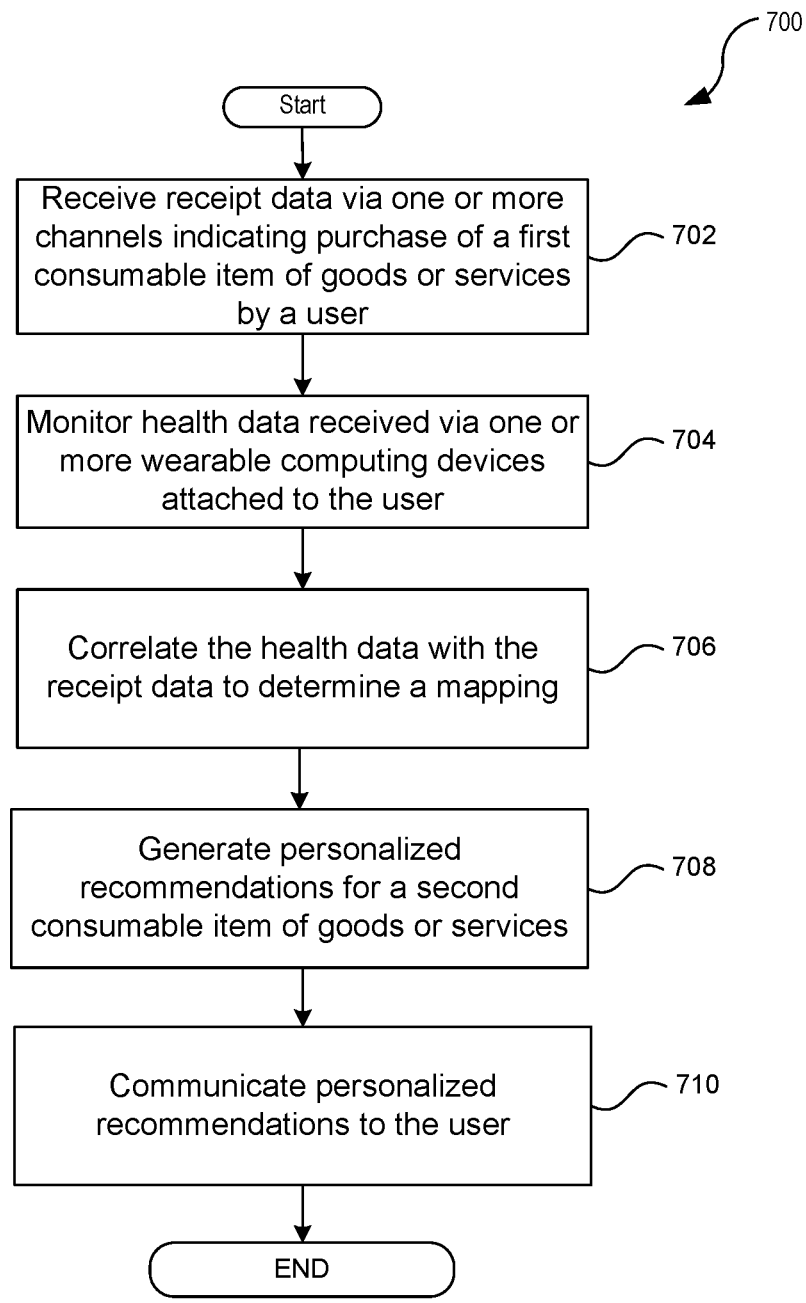
FIG. 7 is a flowchart illustrating a set of operations for receipt data use from the perspective of a server, in accordance with various embodiments of the disclosure.

FIG. 7 is a flowchart illustrating a set of operations 700 for generating personalized recommendations for a user based on health data monitored by a wearable device attached to the body of a user. Receiving operation 702 receives receipt data via one or more channels, the receipt indicating purchase of a first consumable item of goods or services by a user. Examples of channels can be a short message service (SMS) message, a multimedia message service (MMS) message, or an email message. A receipt can be sent electronically to receipt data manager platform 120 by a user, or by a merchant associated with the purchased goods or services, or by both the user and the merchant.

Monitoring operation 704 monitors the health-related data of a user via a wearable device attached to or associated with the user. The wearable device can be, for example, a band or necklace attached to a user's body. In some instances, the wearable device can be a user's mobile phone. The wearable device can send vital health data or fitness/physical exercise data directly to the receipt data manager platform 120, or it can send such data to a user's mobile device, which then conveys this data to the receipt data manager platform 120. In some embodiments, receipt data manager platform 120 tracks a user's exercise levels (e.g., number of steps walked, number of calories burned, number of miles ran/biked/swam, amount of weight lifted during a workout, number of repetitions and sets of an exercise performed, a time duration of the exercise, a type of exercise, heartrate, body weight, body density, and pulse). In some instances, receipt data manager platform 120 can receive real-time or near real-time data corresponding to a user's health and fitness levels, either directly entered by a user or tracked by a wearable device attached to the user's body.

Correlating operation 706 correlates the health data received from the wearable device with the receipt data to generate a mapping between the health of the user and the purchase habit of the first consumable item of goods or services. Generating operation 708 generates personalized recommendations for a second consumable item of goods or services, based on the mapping created as an outcome of the correlating operation 706. Communicating operation 710 communicates the personalized recommendations to the user. This facilitates the user to opt for healthier choices of food and beverages based on analysis of purchase habits of a user in view of the user's health-related data. The outcome of the correlation can be in the form of graphs and/or statistics.

Computer System Overview

Figure 8:
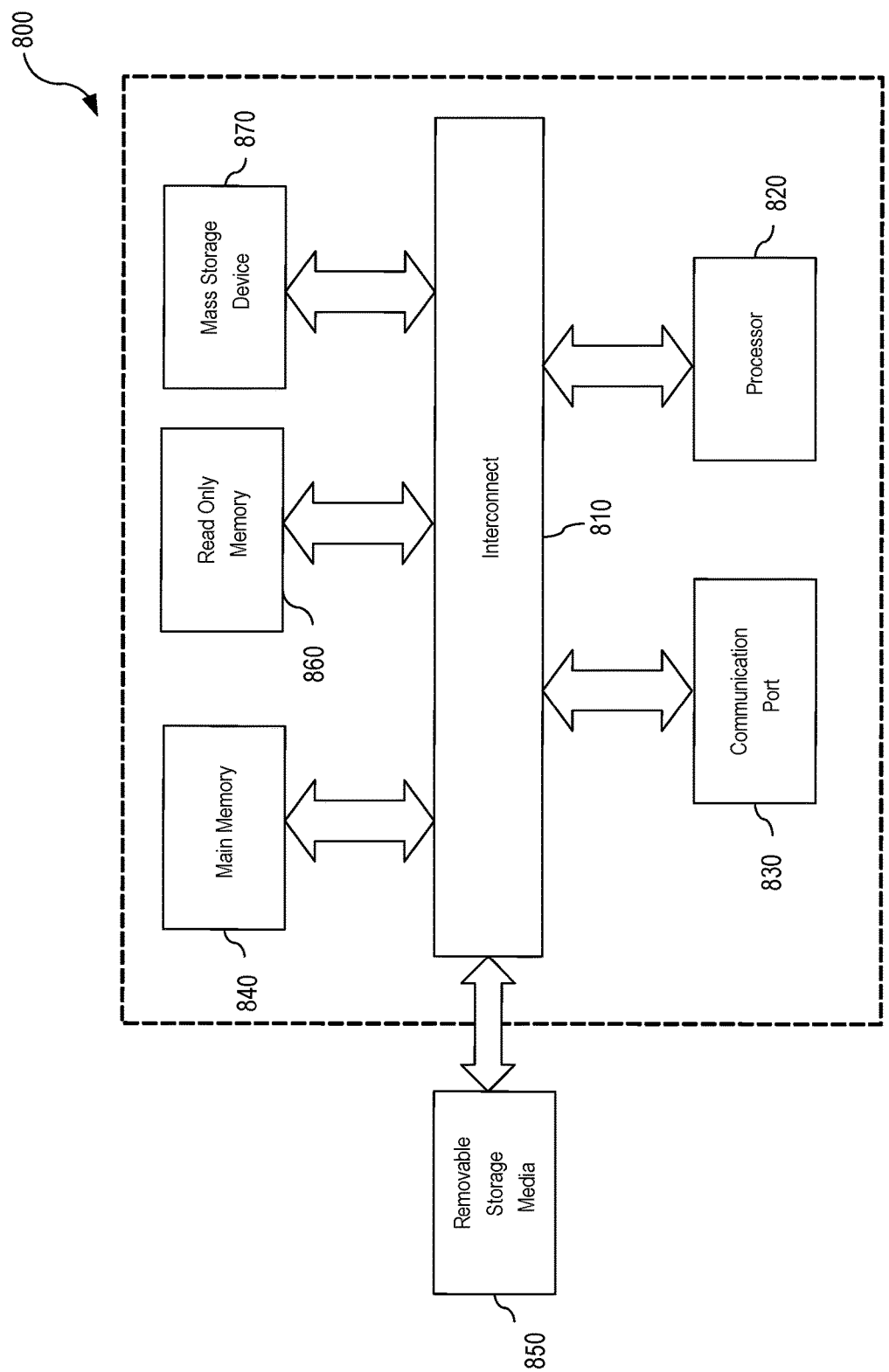
FIG. 8 illustrates an example of a computer system with which some embodiments of the present disclosure may be used.
Figure 9:
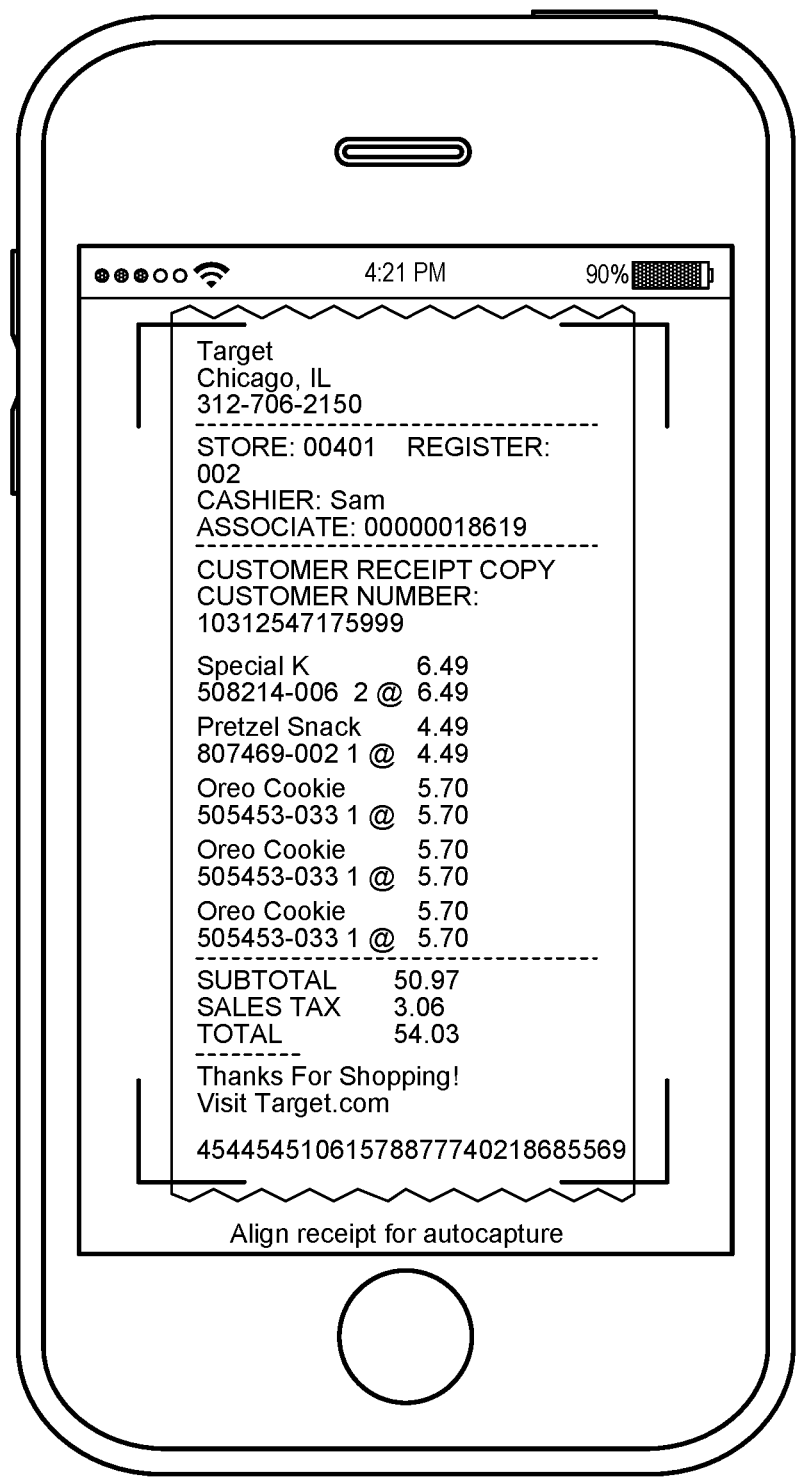
FIGS. 9-33 illustrate various graphical user interfaces (GUI's) in accordance with various embodiments of the disclosure.
Figure 10:
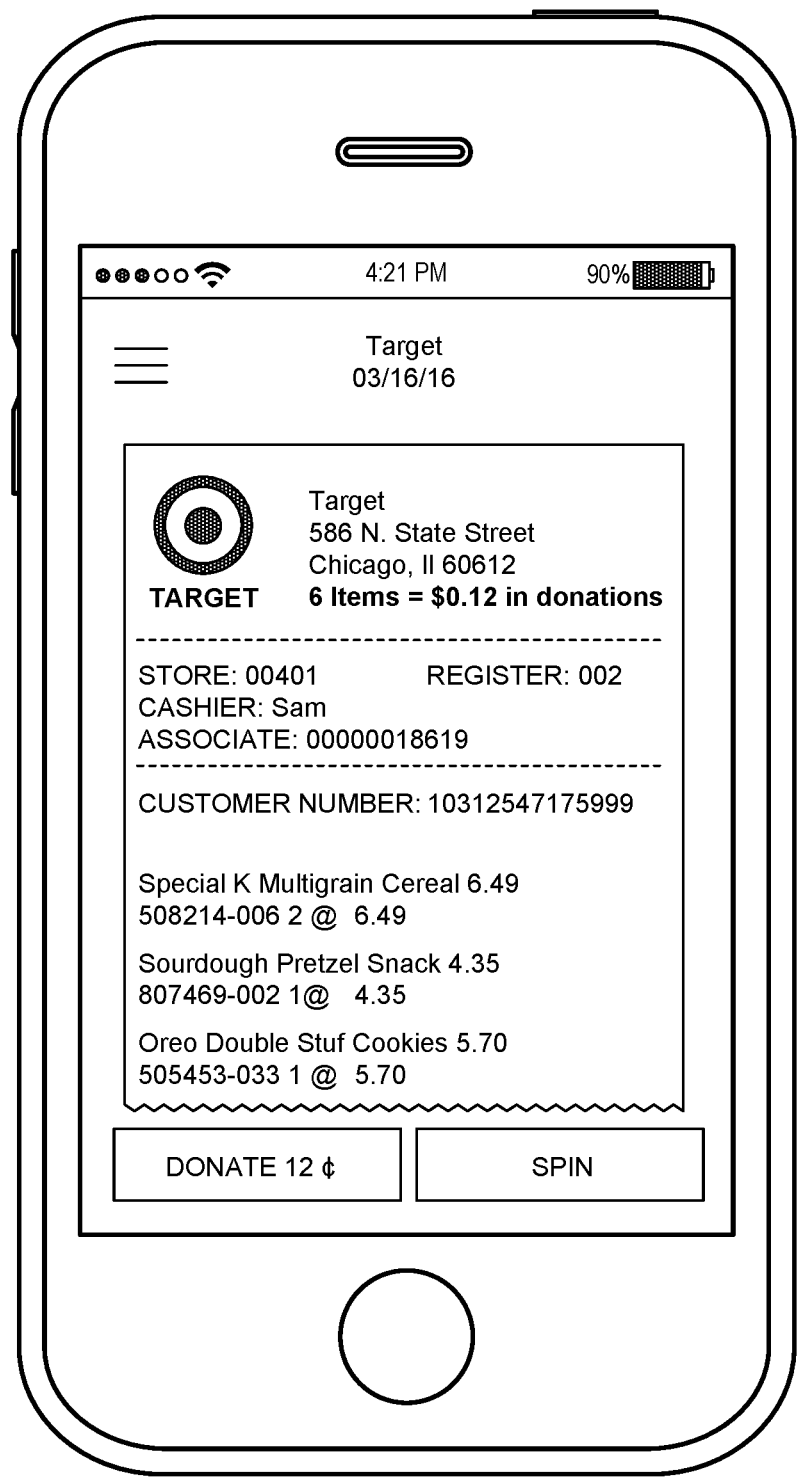

Embodiments of the present disclosure include various steps and operations, which have been described above. A variety of these steps and operations may be performed by hardware components or may be embodied in machine-executable instructions, which may be used to cause a general-purpose or special-purpose processor programmed with the instructions to perform the steps. Alternatively, the steps may be performed by a combination of hardware, software, and/or firmware. As such, FIG. 8 is an example of a computer system 800 with which embodiments of the present disclosure may be utilized. According to the present example, the computer system includes an interconnect 810, at least one processor 820, at least one communication port 830, a main memory 840, a removable storage media 850, a read only memory 860, and a mass storage device 870.

Processor(s) 820 can be any known processor, such as, but not limited to, an Intel® Itanium® or Itanium 2® processor(s), or AMD® Opteron® or Athlon MP® processor(s), or Motorola® lines of processors. Communication port(s) 830 can be any of an RS-232 port for use with a modem-based dialup connection, a 10/100 Ethernet port, or a Gigabit port using copper or fiber. Communication port(s) 830 may be chosen, depending on a network such a Local Area Network (LAN), Wide Area Network (WAN), or any network to which the computer system 800 connects.

Main memory 840 can be Random Access Memory (RAM) or any other dynamic storage device(s) commonly known in the art. Read only memory 860 can be any static storage device(s), such as Programmable Read Only Memory (PROM) chips for storing static information, such as instructions for processor 820.

Mass storage device 870 can be used to store information and instructions. For example, hard disks such as the Adaptec® family of SCSI drives, an optical disc, an array of disks such as RAID, the Adaptec family of RAID drives, or any other mass storage devices may be used.

Interconnect 810 communicatively couples processor(s) 820 with the other memory, storage, and communication blocks. Interconnect 810 can be a PCI/PCI-X- or SCSI-based system bus, depending on the storage devices used.

Removable storage media 850 can be any kind of external hard drives, floppy drives, IOMEGA® Zip Drives, Compact Disc-Read Only Memory (CD-ROM), Compact Disc-Re-Writable (CD-RW), or Digital Video Disc-Read Only Memory (DVD-ROM).

The components described above are meant to exemplify some types of possibilities. In no way should the aforementioned examples limit the disclosure, as they are only exemplary embodiments.

Terminology

Brief definitions of terms, abbreviations, and phrases used throughout this application are given below.

The terms "connected" or "coupled" and related terms are used in an operational sense and are not necessarily limited to a direct physical connection or coupling. Thus, for example, two devices may be coupled directly or via one or more intermediary media or devices. As another example, devices may be coupled in such a way that information can be passed therebetween, while not sharing any physical connection with one another. Based on the disclosure provided herein, one of ordinary skill in the art will appreciate a variety of ways in which connection or coupling exists in accordance with the aforementioned definition.

The phrases "in some embodiments," "according to some embodiments," "in the embodiments shown," "in other embodiments," "embodiments," and the like generally mean that the particular feature, structure, or characteristic following the phrase is included in at least one embodiment of the present disclosure and may be included in more than one embodiment of the present disclosure. In addition, such phrases do not necessarily refer to the same embodiments or to different embodiments.

If the specification states a component or feature "may," "can," "could," or "might" be included or have a characteristic, that particular component or feature is not required to be included or have the characteristic.

The term "responsive" includes completely or partially responsive.

The term "module" refers broadly to a software, hardware, or firmware (or any combination thereof) component. Modules are typically functional components that can generate useful data or other output using specified input(s). A module may or may not be self-contained. An application program (also called an "application") may include one or more modules, or a module can include one or more application programs.

The term "network" generally refers to a group of interconnected devices capable of exchanging information. A network may be as few as several personal computers on a Local Area Network (LAN) or as large as the Internet, a worldwide network of computers. As used herein, "network" is intended to encompass any network capable of transmitting information from one entity to another. In some cases, a network may be comprised of multiple networks, even multiple heterogeneous networks, such as one or more border networks, voice networks, broadband networks, financial networks, service provider networks, Internet Service Provider (ISP) networks, and/or Public Switched Telephone Networks (PSTNs) interconnected via gateways operable to facilitate communications between and among the various networks.

Also, for the sake of illustration, various embodiments of the present disclosure have herein been described in the context of computer programs, physical components, and logical interactions within modern computer networks. Importantly, while these embodiments describe various embodiments of the present disclosure in relation to modern computer networks and programs, the method and apparatus described herein are equally applicable to other systems, devices, and networks, as one skilled in the art will appreciate. As such, the illustrated applications of the embodiments of the present disclosure are not meant to be limiting, but instead are examples. Other systems, devices, and networks to which embodiments of the present disclosure are applicable include, but are not limited to, other types of communication and computer devices and systems. More specifically, embodiments are applicable to communication systems, services, and devices such as cell phone networks and compatible devices. In addition, embodiments are applicable to all levels of computing, from the personal computer to large network mainframes and servers.

In conclusion, the present disclosure discloses novel systems, methods, and arrangements for receipt data use. While detailed descriptions of one or more embodiments of the disclosure have been given above, various alternatives, modifications, and equivalents will be apparent to those skilled in the art without varying from the spirit of the disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof. Therefore, the above description should not be taken as limiting.

What is claimed is:

1. A method implemented by a server, the method comprising:
    capturing, via a mobile device running a mobile application, receipt data indicating a purchase, of a first consumable item of goods or services by a user;
    assigning a health score based on the user purchasing the first consumable item;
    establishing, via a low energy signal within a store, a connection with the mobile device;
    detecting, via the mobile application running on the mobile device, a location of the user within the store, by detecting wireless communication signals broadcasted at an entrance or exit of an aisle within the store, wherein the store contains a second consumable item of goods or services;
    receiving, via one or more wearable computing devices attached to the user within the store, continuously captured health data including an exercise level of the user;
    correlating the health data with the receipt data to determine a mapping between a health of the user within the store and a purchase habit of the first consumable item of goods or services;
    generating, for the user within the store, a real-time in-store recommendation to swap the first consumable item with the second consumable item,
        wherein the real-time in-store recommendation identifies the first consumable item and the second consumable item, and
        wherein the real-time in-store recommendation is based on A) the second consumable item containing different ingredients than the first consumable item, B) the mapping between the health of the user and the purchase habit, and C) the location of the user within the store;
    communicating, to the mobile device of the user within the store, the real-time in-store recommendation for the second consumable item of goods or services with a price of the second consumable item;
    updating the health score based on the user purchasing the second consumable item containing different ingredients than the first consumable item; and
    communicating, to a computing device of an insurance provider, the updated health score based on the user purchasing the second consumable item, wherein the insurance provider offers discounted insurance to the user based on the updated health score.

2. The method of claim 1, wherein the health data includes at least one of a number of steps walked, a number of calories burned, a number of miles ran, a number of miles biked, a number of miles swam, an amount of weight lifted during a workout, a number of repetitions and sets of an exercise performed, a time duration of the exercise, heart-rate, body weight, body density, pulse, or a type of exercise.

3. The method of claim 1, wherein correlating the health data with the receipt data to determine the mapping between the health of the user and the purchase habit of the first consumable item of goods or services includes:
    generating a custom list for the user, the custom list including information relating to at least one of: options for healthy food and beverage, options for exercise, or options for leading a healthy stress-free life.

4. The method of claim 1, further comprising:
    communicating, to a health insurance provider of the user, the mapping between the health of the user and the purchase habit of the first consumable item of goods or services.

5. The method of claim 1, wherein the mapping between the health of the user and the purchase habit of the first consumable item of goods or services is used to provide discounts on health insurance or life insurance policies.

6. The method of claim 1, further comprising:
    generating a custom list for the user based on an analysis of historical purchase habits of the user, the historical purchase habits included in data collected from prior receipts of consumable items of goods or services.

7. The method of claim 1, further comprising:
    detecting information identifying a purchase context associated with the first consumable item of goods or services via the mobile device of the user.

8. The method of claim 1, further comprising:
    detecting information identifying a purchase context associated with the first consumable item of goods or services via the mobile device of the user, wherein a wireless communication signal broadcasted by a device located external to the mobile device of the user generates the information identifying the purchase context.

9. The method of claim 8, wherein the purchase context includes at least one of: a time, the store, goods or services, and types of goods or services, wherein the method further comprises:
    receiving reviews of consumable items of goods or services from the user.

10. A non-transitory computer-readable storage medium storing instructions that, when executed by a computing system, cause the computing system to perform a process comprising:
    capturing, via a mobile device running a mobile application, receiving receipt data indicating a purchase, of a first consumable item of goods or services by a user;
    assigning a health score based on the user purchasing the first consumable item;

establishing, via a low energy signal within a store, a connection with the mobile device;

detecting, via the mobile application running on the mobile device, a location of the user within the store, by detecting wireless communication signals broadcasted at an entrance or exit of an aisle within the store, wherein the store contains a second consumable item of goods or services;

receiving, via one or more wearable computing devices attached to the user within the store, continuously captured health data including an exercise level of the user;

correlating the health data with the receipt data to determine a mapping between a health of the user within the store and a purchase habit of the first consumable item of goods or services;

generating, for the user within the store, a real-time in-store recommendation to swap the first consumable item with the second consumable item,
wherein the real-time in-store recommendation identifies the first consumable item and the second consumable item, and
wherein the real-time in-store recommendation is based on A) the second consumable item containing different ingredients than the first consumable item, B) the mapping between the health of the user and the purchase habit, and C) the location of the user within the store;

communicating, to the mobile device of the user within the store, the real-time in-store recommendation for the second consumable item of goods or services with a price of the second consumable item;

updating the health score based on the user purchasing the second consumable item containing different ingredients than the first consumable item; and communicating, to a computing device of an insurance provider, the updated health score based on the user purchasing the second consumable item, wherein the insurance provider offers discounted insurance to the user based on the updated health score.

11. The non-transitory computer-readable storage medium of claim 10, wherein correlating the health data with the receipt data to determine the mapping between the health of the user and the purchase habit of the first consumable item of goods or services includes:
generating a custom list for the user, the custom list including information relating to at least one of: options for healthy food and beverage, options for exercise, or options for leading a healthy stress-free life.

12. The non-transitory computer-readable storage medium of claim 10, wherein the process further comprises:
communicating, to a health insurance provider of the user, the mapping between the health of the user and the purchase habit of the first consumable item of goods or services.

13. The non-transitory computer-readable storage medium of claim 10, wherein the mapping between the health of the user and the purchase habit of the first consumable item of goods or services is used to provide discounts on health insurance or life insurance policies.

14. The non-transitory computer-readable storage medium of claim 10, wherein the process further comprises:
generating a custom list for the user based on an analysis of historical purchase habits of the user, the historical purchase habits included in data collected from prior receipts of consumable items of goods or services.

15. The non-transitory computer-readable storage medium of claim 10, wherein the process further comprises:
detecting information identifying a purchase context associated with the first consumable item of goods or services via the mobile device of the user,
wherein a wireless communication signal broadcasted by a device located external to the mobile device of the user generates the information identifying the purchase context, and
wherein the purchase context includes at least one of: a time, the store, goods or services, and types of goods or services.

16. A computing system comprising:
one or more processors; and
one or more memories storing instructions that, when executed by the one or more processors, cause the computing system to perform a process comprising:
capturing, via a mobile device running a mobile application, receipt data indicating a purchase, of a first consumable item of goods or services by a user;
assigning a health score based on the user purchasing the first consumable item;
establishing, via a low energy signal within a store, a connection with the mobile device;
detecting, via the mobile application running on the mobile device, a location of the user within the store, by detecting wireless communication signals broadcasted at an entrance or exit of an aisle within the store, wherein the store contains a second consumable item of goods or services;
receiving, via one or more wearable computing devices attached to the user within the store, continuously captured health data including an exercise level of the user;
correlating the health data with the receipt data to determine a mapping between a health of the user within the store and a purchase habit of the first consumable item of goods or services;
generating, for the user within the store, a real-time in-store recommendation to swap the first consumable item with the second consumable item,
wherein the real-time in-store recommendation identifies the first consumable item and the second consumable item, and
wherein the real-time in-store recommendation is based on A) the second consumable item containing different ingredients than the first consumable item, B) the mapping between the health of the user and the purchase habit, and C) the location of the user within the store;
communicating, to the mobile device of the user within the store, the real-time in-store recommendation for the second consumable item of goods or services with a price of the second consumable item;
updating the health score based on the user purchasing the second consumable item containing different ingredients than the first consumable item; and
communicating, to a computing device of an insurance provider, the updated health score based on the user purchasing the second consumable item, wherein the insurance provider offers discounted insurance to the user based on the updated health score.

17. The system of claim 16, wherein correlating the health data with the receipt data to determine the mapping between the health of the user and the purchase habit of the first consumable item of goods or services includes:

generating a custom list for the user, the custom list including information relating to at least one of: options for healthy food and beverage, options for exercise, or options for leading a healthy stress-free life.

18. The system of claim 16, wherein the mapping between the health of the user and the purchase habit of the first consumable item of goods or services is used to provide discounts on health insurance or life insurance policies.

19. The method of claim 1, further comprising:
- detecting information identifying a purchase context associated with the first consumable item of goods or services via the mobile device of the user,
  - wherein a wireless communication signal broadcasted by a device located external to the mobile device of the user generates the information identifying the purchase context,
  - wherein the purchase context includes at least one of: a time, the store, goods or services, and types of goods or services, and
  - wherein the mobile device captures the receipt data by using a camera to capture an image of a receipt indicating the purchase of the first consumable item of goods or services.

* * * * *